US012616458B2

(12) United States Patent
Hioki

(10) Patent No.: US 12,616,458 B2
(45) Date of Patent: May 5, 2026

(54) ADHESIVE MATERIAL INJECTION DEVICE

(71) Applicant: TERUMO KABUSHIKI KAISHA, Tokyo (JP)

(72) Inventor: Yuichi Hioki, Fuji (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 168 days.

(21) Appl. No.: 18/458,293

(22) Filed: Aug. 30, 2023

(65) Prior Publication Data

US 2023/0404557 A1 Dec. 21, 2023

Related U.S. Application Data

(63) Continuation of application No. PCT/JP2022/010496, filed on Mar. 10, 2022.

(30) Foreign Application Priority Data

Mar. 29, 2021 (JP) ................................. 2021-054840

(51) Int. Cl.
*A61B 17/00* (2006.01)
*A61B 17/12* (2006.01)

(52) U.S. Cl.
CPC ................... *A61B 17/00491* (2013.01); *A61B 2017/00778* (2013.01); *A61B 2017/12004* (2013.01)

(58) Field of Classification Search
None
See application file for complete search history.

(56) References Cited

U.S. PATENT DOCUMENTS 5,431,639 A 7/1995 Shaw
6,033,427 A * 3/2000 Lee ..................... A61B 17/0057
604/59

(Continued)

FOREIGN PATENT DOCUMENTS

JP H09504444 A 5/1997
JP 2011508626 A 3/2011

(Continued)

OTHER PUBLICATIONS

English Translations of the International Search Report (Form PCT/ISA/210) and the Written Opinion of the International Searching Authority (Form PCT/ISA/237) issued May 24, 2022, by the Japan Patent Office in corresponding International Application No. PCT/JP2022/010496. (6 pages).

(Continued)

*Primary Examiner* — Shaun L David
(74) *Attorney, Agent, or Firm* — Buchanan Ingersoll & Rooney PC

(57) ABSTRACT

An adhesive material injection device that indwells an adhesive material at an appropriate position with respect to a puncture site formed in a living body lumen. The adhesive material injection device includes a tubular member including a plurality of lumens and an adhesive material configured to be held in the lumen of the tubular member. The tubular member includes a first lumen extending between a first distal opening and a first proximal opening, and a second lumen extending between the second distal opening and the second proximal opening at a position different from the first lumen. The first distal opening is located on a distal side relative to the second distal opening in a longitudinal direction of the tubular member. The adhesive material is configured to be held in the first lumen between the first distal opening and the first proximal opening.

19 Claims, 15 Drawing Sheets

(56)          References Cited

U.S. PATENT DOCUMENTS

| | | | | | |
|---|---|---|---|---|---|
| 6,334,865 | B1* | 1/2002 | Redmond | .......... | A61B 17/0057 |
| | | | | | 606/139 |
| 6,475,177 | B1 | 11/2002 | Suzuki | | |
| 2002/0006429 | A1* | 1/2002 | Redmond | .......... | A61B 17/0057 |
| | | | | | 424/443 |
| 2002/0026215 | A1* | 2/2002 | Redmond | .......... | A61B 17/0057 |
| | | | | | 606/213 |
| 2003/0097149 | A1* | 5/2003 | Edwards | .......... | A61B 17/00491 |
| | | | | | 606/214 |
| 2003/0191496 | A1* | 10/2003 | Edwards | .............. | A61B 18/148 |
| | | | | | 606/213 |
| 2009/0171282 | A1 | 7/2009 | Pipenhagen et al. | | |
| 2011/0178399 | A1 | 7/2011 | Del | | |
| 2013/0190812 | A1* | 7/2013 | Vidlund | ............. | A61B 17/0057 |
| | | | | | 606/213 |
| 2013/0190813 | A1* | 7/2013 | Tegels | ................ | A61B 17/0057 |
| | | | | | 606/214 |
| 2013/0253576 | A1* | 9/2013 | Parsonage | ........ | A61B 17/00491 |
| | | | | | 606/213 |
| 2013/0269299 | A1* | 10/2013 | Parsonage | ........ | A61B 17/00491 |
| | | | | | 53/476 |
| 2014/0058440 | A1* | 2/2014 | Tegels | ................ | A61B 17/0057 |
| | | | | | 606/213 |
| 2014/0058441 | A1 | 2/2014 | Tegels et al. | | |
| 2014/0121698 | A1* | 5/2014 | Kirk | ................... | A61B 17/0057 |
| | | | | | 606/213 |
| 2014/0135825 | A1 | 5/2014 | Tegels et al. | | |
| 2014/0135831 | A1* | 5/2014 | White | ................ | A61B 17/0057 |
| | | | | | 606/214 |
| 2014/0236224 | A1* | 8/2014 | Tegels | ................ | A61B 17/0057 |
| | | | | | 606/213 |
| 2014/0236225 | A1* | 8/2014 | Tegels | ................ | A61B 17/0057 |
| | | | | | 606/213 |
| 2014/0257371 | A1* | 9/2014 | Tegels | ................ | A61B 17/0057 |
| | | | | | 606/213 |
| 2021/0038210 | A1 | 2/2021 | Lamazouade et al. | | |

FOREIGN PATENT DOCUMENTS

| | | | |
|---|---|---|---|
| JP | 2011530362 A | 12/2011 | |
| WO | 0030553 A1 | 6/2000 | |
| WO | 2019206998 A1 | 10/2019 | |

OTHER PUBLICATIONS

International Search Report (PCT/ISA/210) with English translation and Written Opinion (PCT/ISA/237) mailed on May 24, 2022, by the Japanese Patent Office as the International Searching Authority for International Application No. PCT/JP2022/010496.

* cited by examiner

ADHESIVE MATERIAL INJECTION DEVICE

CROSS-REFERENCES TO RELATED APPLICATIONS

This application is a continuation of International Application No. PCT/JP2022/010496 filed on Mar. 10, 2022, which claims priority to Japanese Application No. 2021-054840 filed on Mar. 29, 2021, the entire content of both of which is incorporated herein by reference.

TECHNOLOGICAL FIELD

The present disclosure generally relates to an adhesive material injection device.

BACKGROUND DISCUSSION

In the related art, there has been known a procedure of introducing various medical elongated bodies (for example, introducer sheaths) into a blood vessel through a puncture site formed in the blood vessel of a limb such as an arm of a patient and performing treatment and therapy on a lesion site. When such a procedure is performed, a surgeon performs hemostasis on the puncture site when removing the medical elongated body from the puncture site.

As one of hemostasis methods, there is known a compression hemostasis method of applying a compressive force to the puncture site of the blood vessel or a subcutaneous tissue around the puncture site from a living body surface layer side of the patient. However, when the compression hemostasis method is adopted, blood vessel occlusion may occur when excessive compression, which means the compressive force is excessively large, is performed for a long time. Therefore, the surgeon is required to appropriately adjust the compressive force.

Concerning such a technical problem, the following International Patent Application Publication No. WO00/030553 discloses a hemostatic device that enables non-compression hemostasis. The hemostatic device in International Patent Application Publication No. WO00/030553 includes a sheath insertable into a living body and a cartridge charged with a hemostasis agent held inside the sheath. In a procedure using the hemostatic device in International Patent Application Publication No. WO00/030553, the surgeon introduces a distal opening of the sheath to the periphery of the puncture site of the blood vessel and discharges the hemostasis agent through the distal opening. The surgeon can close the puncture site by disposing the hemostasis agent discharged from the sheath around the puncture site of the blood vessel.

The above hemostatic device includes a stopper (locking member) that helps prevent a distal portion of the sheath from being inserted beyond a depth of the puncture site of the blood vessel. The stopper is mounted on an outer peripheral surface of the sheath, and when the sheath is inserted into the living body, the stopper comes into contact with the living body surface layer of the patient to limit an insertion length of the sheath.

According to the above hemostatic device, the sheath can be prevented from being excessively inserted into the blood vessel beyond the depth of the puncture site of the blood vessel. However, when the above hemostatic device is used, the surgeon cannot grasp an accurate position of the puncture site of the blood vessel when starting the discharge of the hemostasis agent. Therefore, the surgeon needs to dispose the distal opening of the sheath at the puncture site of the blood vessel depending on a hand feeling. Therefore, in the procedure using the hemostatic device, it can be difficult to appropriately position the distal opening of the sheath with respect to the puncture site of the blood vessel.

SUMMARY

An adhesive material injection device is disclosed, which is capable of indwelling an adhesive material at an appropriate position with respect to a puncture site formed in a living body lumen.

An adhesive material injection device according to the present disclosure includes: a tubular member including a plurality of lumens; and an adhesive material held in the lumen of the tubular member. The tubular member includes a first lumen extending between a first distal opening and a first proximal opening and a second lumen extending between a second distal opening and a second proximal opening at a position different from the first lumen. The first distal opening is located on a distal side relative to the second distal opening in a longitudinal direction of the tubular member. The adhesive material is held in the first lumen between the first distal opening and the first proximal opening.

According to the present disclosure, the tubular member has the first distal opening and the second distal opening located on a proximal side of the first distal opening. The adhesive material is held in the first lumen extending between the first distal opening and the first proximal opening. Further, in the adhesive material injection device, the first distal opening through which the adhesive material can be discharged is located on the distal side relative to the second distal opening through which blood can flow in. A puncture foramen formed in a puncture site of a patient for introducing a medical elongated body is formed at an acute angle with respect to a blood vessel from a skin tissue. Therefore, in the adhesive material injection device, in order to position the first distal opening and the second distal opening outside the puncture foramen formed in the blood vessel at the same timing in a state where the second distal opening is located on a peripheral side of the blood vessel relative to the first distal opening, it is necessary to position the first distal opening on the distal side relative to the second distal opening. According to the adhesive material injection device having such a configuration, a surgeon can check a position of the second distal opening while checking leakage of the blood from the second proximal opening by introducing the adhesive material injection device into the blood vessel through the puncture site of the patient, disposing the first distal opening and the second distal opening of the tubular member in the blood vessel, and then retracting the adhesive material injection device to the proximal side. Therefore, by confirming that the blood leaks from the second proximal opening of the tubular member, the surgeon can rather easily grasp whether the first distal opening of the tubular member is located inside a blood vessel wall (in the blood vessel) or outside the blood vessel wall (in a subcutaneous tissue). Therefore, since the surgeon can accurately grasp a discharge position of the adhesive material with respect to periphery of the puncture foramen of the blood vessel, the adhesive material can be indwelled at an appropriate position with respect to the puncture foramen formed in the blood vessel.

An adhesive material injection device according to the present disclosure includes: a tubular member including a first lumen extending between a first distal opening and a first proximal opening of the tubular member and a second lumen extending between a second distal opening and a second proximal opening of the tubular member at a position different from the first lumen; the first distal opening is located on a distal side relative to the second distal opening in a longitudinal direction of the tubular member; and wherein the first lumen is configured to hold an adhesive material between the first distal opening and the first proximal opening.

A medical instrument according to the present disclosure includes: an adhesive material injection device, the adhesive material injection device including a tubular member including a first lumen extending between a first distal opening and a first proximal opening of the tubular member and a second lumen extending between a second distal opening and a second proximal opening of the tubular member at a position different from the first lumen, the first distal opening is located on a distal side relative to the second distal opening in a longitudinal direction of the tubular member, and a hub portion between the first proximal opening and the second proximal opening; an adhesive material configured to be held in the first lumen between the first distal opening and the first proximal opening; and an introduction sheath having a lumen into which the adhesive material injection device is configured to be inserted.

DETAILED DESCRIPTION

Figure 1:
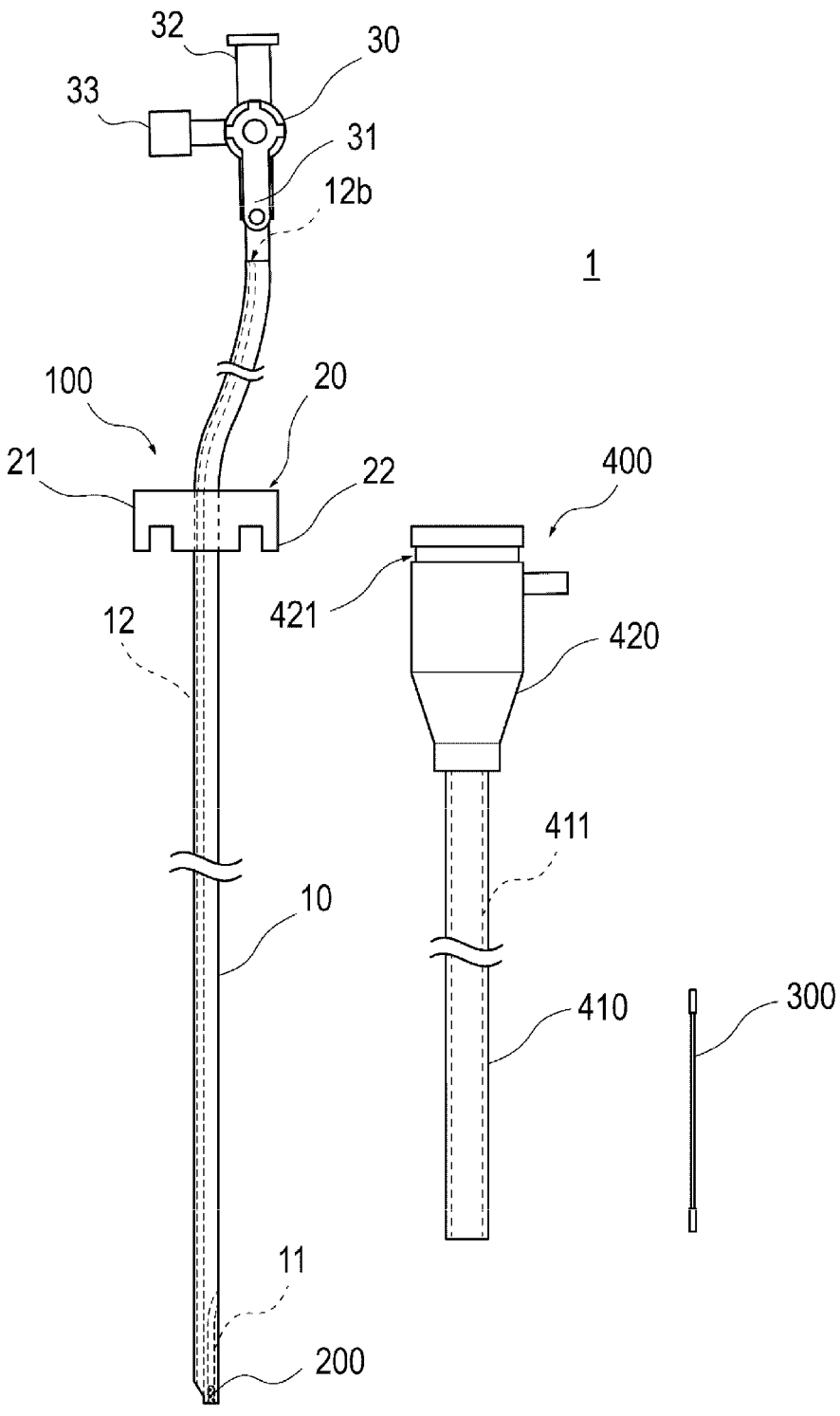
FIG. 1 is a schematic configuration diagram of a medical instrument according to the present embodiment.

Set forth below with reference to the accompanying drawings is a detailed description of embodiments of an adhesive material injection device.

In the drawings attached to the present specification, for convenience of illustration and understanding, a scale, an aspect ratio, a shape, and the like may be changed from actual ones and may be schematically expressed as appropriate, and the drawings are just examples and do not limit the interpretation of the present disclosure.

Note that in the present specification, the description is given by adding an ordinal number such as "first" or "second", but unless otherwise specified, it is used for convenience and does not define any order.

In the description of the present specification, an extending direction of an adhesive material injection device 100 (for example, a vertical direction in FIGS. 1, 2, and 3) is referred to as a "longitudinal axis" (i.e., long-axis direction). A side of the adhesive material injection device 100 to be introduced into a living body is referred to as a "distal end" (lower end sides in FIGS. 1, 2, and 3), and an end side opposite to the distal end (upper-end sides in FIGS. 1, 2, and 3) is referred to as a "proximal end". Terms "distal portion" and "distal side" mean a region including the distal end (most distal end) and a predetermined range from the distal end toward a proximal side, and terms "proximal portion" and "proximal side" mean a region including the proximal end (most proximal end) and a predetermined range from the proximal end toward the distal side.

Figure 2:
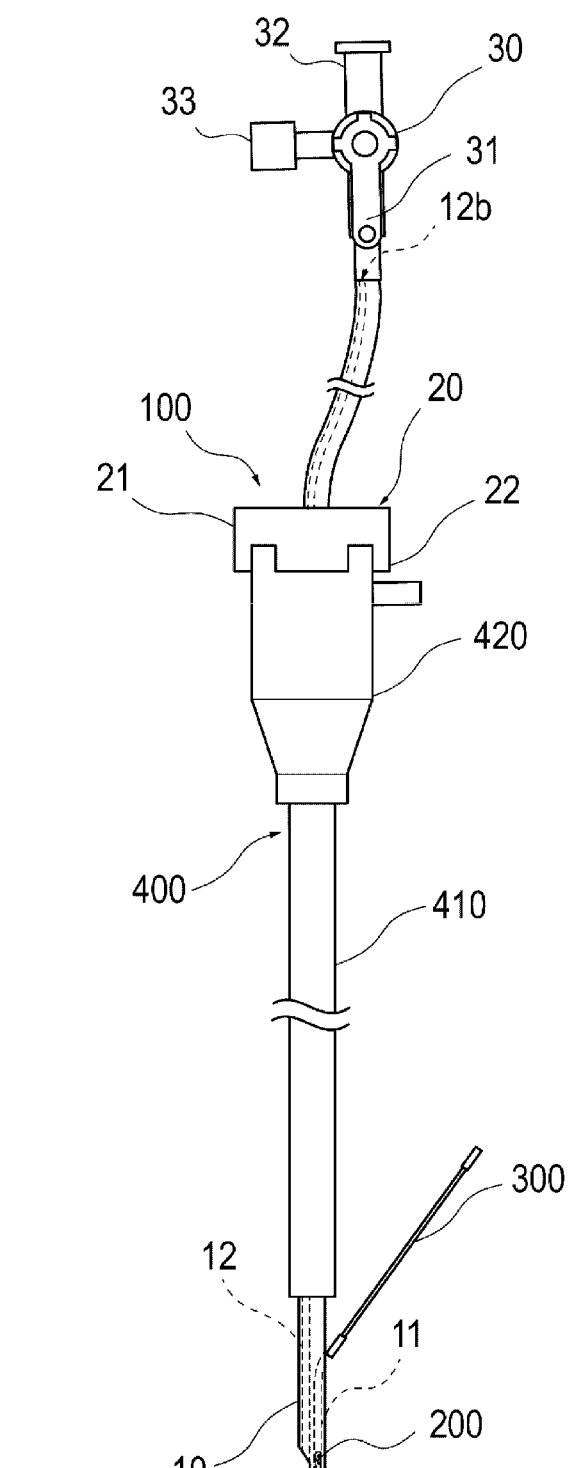
FIG. 2 is a schematic configuration diagram illustrating the medical instrument according to the present embodiment when an adhesive material injection device is mounted on an introducer sheath.

The adhesive material injection device 100 according to an embodiment of the present disclosure can be used for, after extracting a device such as an introduction sheath (introducer sheath 400) indwelled in a puncture site formed in a blood vessel Bv (for example, a radial artery) of a limb such as an arm of a patient which is a living body lumen, performing hemostasis on the puncture site. Note that contents of a specific procedure, a treatment procedure, and the like using the adhesive material injection device 100 according to the embodiment of the present disclosure are representative examples and do not specify the present disclosure. Configuration First, a configuration of a medical instrument 1 according to the present embodiment will be described. As shown in FIGS. 1 and 2, the medical instrument 1 includes the adhesive material injection device 100 and the introducer sheath 400. The adhesive material injection device 100 can include a plurality of lumens and holds an adhesive material 200 in a lumen of the plurality of lumens. The adhesive material injection device 100 further includes a pushing member 300 for discharging the adhesive material 200 held in the lumen of the plurality of lumens from the lumen.

Hereinafter, configurations will be described in detail.

Adhesive Material Injection Device

The adhesive material injection device 100 includes a tubular member 10, a hub portion 20, and a stopcock 30. The tubular member 10 can include a first lumen 11, a second lumen 12, and a first marker portion 13. The adhesive material injection device 100 is inserted into the introduction sheath (introducer sheath 400) introduced into the blood vessel Bv and introduced into the blood vessel Bv (see FIGS. 2 and 7B).

Tubular Member

Figure 3:
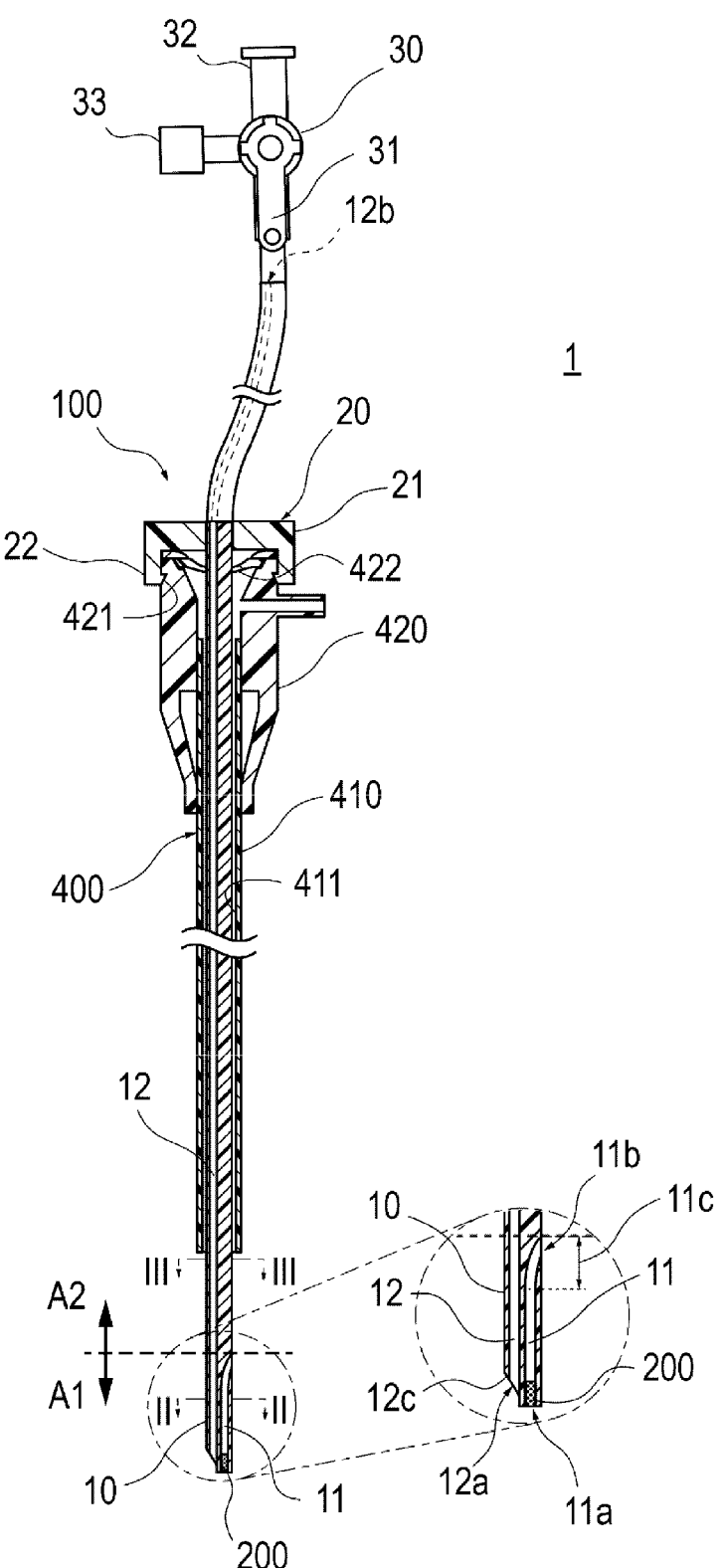
FIG. 3 is a schematic cross-sectional view of the adhesive material injection device according to the present embodiment.

As shown in FIG. 3, the tubular member 10 is a tube that includes the first lumen 11 and the second lumen 12. The first lumen 11 and the second lumen 12 independently extend along the longitudinal direction of the tubular member 10. The adhesive material injection device 100 according to the present embodiment includes two lumens which are the first lumen 11 and the second lumen 12. Note that for example, the tubular member 10 may include three or more lumens when a plurality of the adhesive materials 200 are mixed and used.

An outer diameter and a length of the tubular member 10 are set according to a size (a size of a lumen (French (Fr) size) and a total length of the lumen) of the introducer sheath 400 to be used. Specifically, the outer diameter of the tubular member 10 may be set to a size dedicated to the Fr size (for example, dedicated to a 5 Fr size or a 6 Fr size) of the introducer sheath 400 to be used. Further, the tubular member 10 may be set to cover the Fr size of the introducer sheath 400 to some extent by setting the outer diameter of the tubular member 10 to a minimum size of the Fr size of the introducer sheath 400 that can be used. For example, in a case of "for 5 Fr·6 Fr", the outer diameter of the tubular member 10 is set according to the introducer sheath of 5 Fr size, and in a case of "for 7 Fr·8 Fr", the outer diameter of the tubular member 10 is set according to the introducer sheath of 7 Fr size. The tubular member 10 is set such that a distal end of the tubular member 10 protrudes from a distal end of a sheath main body 410 of the introducer sheath 400. Therefore, the length of the tubular member 10 is set to be longer than a total length of the introducer sheath 400. The tubular member 10 can be set to cover the introducer sheath 400 having different total lengths to some extent by setting a total length of the tubular member 10 to a size exceeding a maximum value of the total length of the introducer sheath 400 that can be used. For example, in a case of "for 7 cm to 15 cm", the total length of the tubular member 10 is set to exceed 15 cm which is the maximum value of the total length of the tubular member 10 that can be used, and in a case of "for 15 cm to 25 cm", the total length of the tubular member 10 is set to exceed 25 cm which is the maximum value of the total length of the tubular member 10 that can be used.

Examples of a constituent material of the tubular member 10 include a resin material such as polypropylene, polyamide, polystyrene, or polyimide. The tubular member 10 is made of a resin material having appropriate hardness and flexibility capable of being deformed along the blood vessel Bv while maintaining lumens of the first lumen 11 and the second lumen 12 after being introduced into the blood vessel Bv. However, specific types of the material constituting the tubular member 10 are not particularly limited.

First Lumen

The first lumen 11 extends between a first distal opening 11a formed on a distal side of the tubular member 10 and a first proximal opening 11b formed on a proximal side of the tubular member 10. The first lumen 11 can be loaded with the adhesive material 200 and functions as an adhesive material discharge lumen for discharging the adhesive material 200 into a puncture foramen P1.

The tubular member 10 has a first region A1 and a second region A2 located on the proximal side relative to the first region A1. As shown in FIG. 3, the first region A1 is a region where the first lumen 11 and the second lumen 12 are present in a cross-section perpendicular to a longitudinal direction of the tubular member 10. Further, the first region A1 is located on the distal side relative to the introducer sheath 400 (that is, a portion not covered with the introducer sheath 400) in a state where the adhesive material injection device 100 is mounted on the introducer sheath 400.

As shown in FIG. 3, the first lumen 11 is formed only in the first region A1 along the longitudinal direction of the tubular member 10. The first region A1 is a region of a predetermined distance from the distal end of the tubular member 10 toward the proximal side. That is, the first lumen 11 is located in the region at a predetermined distance from the distal end of the tubular member 10 toward the proximal side. The first proximal opening 11b of the first lumen 11 is located on the distal side relative to the introducer sheath 400 (that is, a portion not covered with the introducer sheath 400) in a state where the adhesive material injection device 100 is mounted on the introducer sheath 400.

Figure 4A:
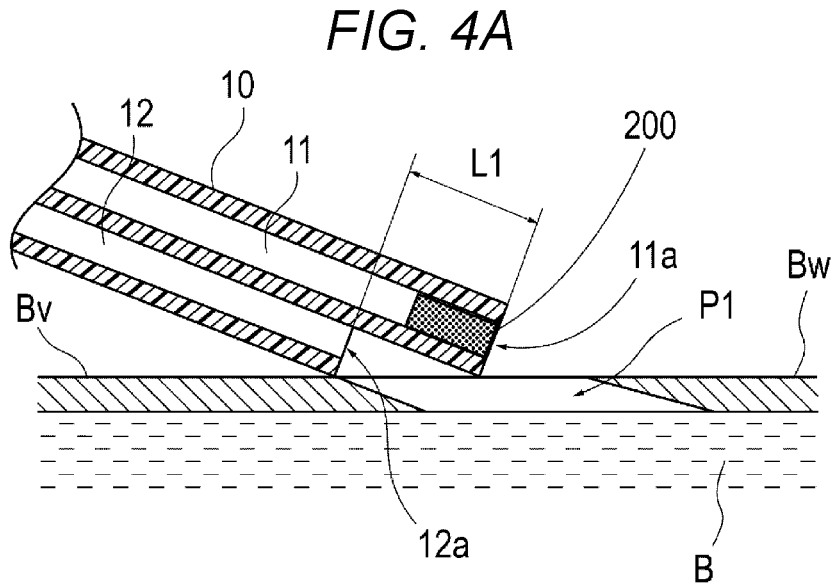
FIG. 4A is a partially enlarged cross-sectional view of the vicinity of a distal end when the adhesive material injection device having a configuration in which there is no inclined portion formed in a second distal opening is pulled out from a blood vessel.
Figure 4B:
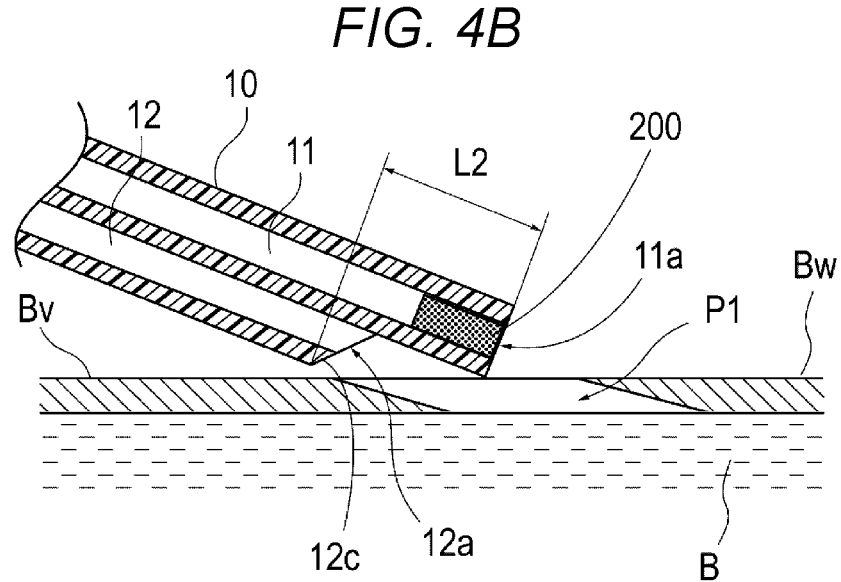
FIG. 4B is a partially enlarged cross-sectional view of the vicinity of the distal end when the adhesive material injection device having a configuration in which the inclined portion is formed in the second distal opening is pulled out from the blood vessel.

As shown in FIGS. 4A and 4B, the first distal opening 11a is located on the distal side (far side) relative to a second distal opening 12a of the second lumen 12 to be described later in the longitudinal direction of the tubular member 10. That is, the first distal opening 11a is shifted to the distal side from a position of the second distal opening 12a (i.e., the first distal opening 11a is distal to the second distal opening 12a). FIG. 4A shows a state where the distal end of the tubular member 10 is located outside a blood vessel wall Bw. The tubular member 10 can have a configuration in which there is no inclined portion 12c to be described later formed in the second distal opening 12a. FIG. 4B shows a state where the distal end of the tubular member 10 is located outside the blood vessel wall Bw. The tubular member 10 has a configuration in which the inclined portion 12c is formed in the second distal opening 12a. Here, the introducer sheath 400 is inserted into the blood vessel Bv, for example, to form 20 degrees to 60 degrees with respect to a body surface (skin) of the patient. That is, the puncture foramen P1 formed in the puncture site of the patient for introducing the introducer sheath 400, for example, is formed at 20 degrees to 60 degrees with respect to the blood vessel Bv from a skin tissue. Therefore, when the surgeon pulls out the adhesive material injection device 100 from the blood vessel Bv, the first distal opening 11a and the second distal opening 12a are located outside the puncture foramen P1 formed in the blood vessel Bv at the same timing, and therefore the first distal opening 11a is preferably located at a position shifted from the position of the second distal opening 12a, for example, by 2 mm to 5 mm on the distal side. That is, in a case of the tubular member 10 shown in FIG. 4A, a length of a distance L1 in the drawing (a distance from a position of an opening end of the second distal opening 12a to a position of an opening end of the first distal opening 11a) is preferably, for example, 2 mm to 5 mm. In a case of the tubular member 10 shown in FIG. 4B, a length of a distance L2 in the drawing (a distance from a position of a proximal end of the inclined portion 12c to a position of an opening end of the first distal opening 11a) is preferably, for example, 2 mm to 5 mm. Further, a center of the first distal opening 11a is formed at a position (eccentric position) deviated from an axial center of the tubular member 10.

In addition, the first distal opening 11a is located on the distal side relative to the second distal opening 12a in the longitudinal direction of the tubular member 10. Therefore, the adhesive material injection device 100 can be obliquely inserted into the blood vessel Bv as shown in FIG. 7D, and can be located at a position where the first distal opening 11a and the second distal opening 12a overlap with each other in an axial direction of the blood vessel Bv around the puncture site in a state where the second distal opening 12a is located on a peripheral side of the blood vessel Bv relative to the first distal opening 11a. Therefore, when the surgeon retreats the adhesive material injection device 100 to the proximal side, the first distal opening 11a and the second distal opening 12a are located outside the blood vessel wall Bw from the puncture foramen P1 at the same timing. Accordingly, the surgeon can check the position of the second distal opening 12a while checking leakage of blood B from a second proximal opening 12b by introducing the adhesive material injection device 100 into the blood vessel Bv through the puncture site of the patient, forming the first distal opening 11a and the second distal opening 12a of the tubular member 10 in the blood vessel Bv, and then retracting the adhesive material injection device 100 to the proximal side. Accordingly, by confirming that the blood B leaks from the second proximal opening 12b of the tubular member 10, the surgeon can rather easily grasp a situation in which the first distal opening 11a of the tubular member 10 is located inside the blood vessel wall Bw (in the blood vessel Bv) or outside the blood vessel wall Bw (in a subcutaneous tissue S). Therefore, since the surgeon can rather accurately grasp a discharge position of the adhesive material 200 with respect to the periphery of the puncture foramen P1 of the blood vessel Bv, the adhesive material 200 can be indwelled at an appropriate position with respect to the puncture foramen P1 formed in the blood vessel Bv. Note that the introducer sheath 400 can be obliquely inserted into the blood vessel Bv to form an access path for introducing a treatment device into the blood vessel Bv from an outside of the living body. Therefore, the puncture foramens P1 and P2 formed in the puncture site of the patient can be formed at an acute angle with respect to the blood vessel Bv from a skin tissue. The peripheral side of the blood vessel Bv is a direction in which the blood B flows.

The first proximal opening 11b is located between the second distal opening 12a and the second proximal opening 12b in the longitudinal direction of the tubular member 10. Further, the first proximal opening 11b is located in the first region A1 and is provided in a side wall of the tubular member 10. Therefore, the first proximal opening 11b is located on the distal side relative to the introducer sheath 400 (that is, a portion not covered with the introducer sheath 400) in the state where the adhesive material injection device 100 is mounted on the introducer sheath 400. Therefore, the surgeon can insert the pushing member 300 into the first proximal opening 11b in the state where the adhesive material injection device 100 is mounted on the introducer sheath 400.

The first proximal opening 11b is exposed to the outside of the living body in a state where the first distal opening 11a is formed in an outer surface of the puncture foramen P1 of the blood vessel Bv (outside the blood vessel wall Bw).

Therefore, the first proximal opening 11b is exposed to the outside of the living body before the first distal opening 11a is located outside the blood vessel wall Bw by simultaneously moving (retracting) the adhesive material injection device 100 and the introducer sheath 400 to the proximal side. The surgeon can discharge the adhesive material 200 to the outside of the blood vessel wall Bw through the first distal opening 11a by inserting the pushing member 300 into the first proximal opening 11b, which is exposed to the outside of the living body.

As shown in FIG. 3, the first lumen 11 is shorter than the second lumen 12. Therefore, the adhesive material injection device 100 can be implemented such that a length of the pushing member 300 to be inserted into the first lumen 11 is shorter than the total length of the tubular member 10. For example, when the tubular member 10 has the first proximal opening 11b and the second proximal opening 12b at the same position on the proximal side of the tubular member 10, the first lumen 11 and the pushing member 300 need to have a device length corresponding to the length of the introducer sheath 400. As the length of the pushing member 300 increases, operability may decrease, and a discharge operation may become complicated. In contrast, since the adhesive material injection device 100 can be implemented such that the length of the pushing member 300 to be inserted into the first lumen 11 is reduced, the surgeon can efficiently transmit a pushing force to the adhesive material 200 when pushing out the adhesive material 200 through the first distal opening 11a.

As shown in FIG. 3, the first proximal opening 11b is located between the second distal opening 12a and the second proximal opening 12b of the tubular member 10, and opens in a side surface of the tubular member 10. In addition, the first proximal opening 11b is located on the distal side relative to the introducer sheath 400 in the state where the adhesive material injection device 100 is mounted on the introducer sheath 400. Therefore, the adhesive material injection device 100 can set the length of the pushing member 300 regardless of the length of the introducer sheath 400. Since the first proximal opening 11b is located between the second distal opening 12a and the second proximal opening 12b, the surgeon can discharge the adhesive material 200 through the first distal opening 11a while checking the leakage of the blood B from the second proximal opening 12b.

The tubular member 10 can have a curved region 11c that forms a part of the first lumen 11 connecting the first distal opening 11a and the first proximal opening 11b. Therefore, the first lumen 11 is curved in a direction of the side surface of the tubular member 10 at a position between the first distal opening 11a and the first proximal opening 11b and at a position on the proximal side relative to a portion where the adhesive material 200 is disposed. The curved region 11c supports a part of the pushing member 300 when the surgeon inserts the pushing member 300 into the first lumen 11 and pushes out the adhesive material 200. Therefore, the surgeon can rather easily transmit to the pushing member 300, a pressing force when the adhesive material 200 is pushed out by the pushing member 300 and can reliably discharge the adhesive material 200.

Note that in FIG. 3, the curved region 11c forms a lumen curved at a predetermined curvature from the first proximal opening 11b toward the first distal opening 11a. However, for example, the curved region 11c may form a lumen that extends obliquely and linearly from the first proximal opening 11b toward an inside of the tubular member 10 and then bends at a predetermined angle.

Second Lumen

The second lumen 12 extends between the second distal opening 12a formed on the distal side of the tubular member 10 and the second proximal opening 12b formed on the proximal side of the tubular member 10. The second lumen 12 can function as, in a state of being introduced into the blood vessel Bv, a reverse blood checking lumen for checking the leakage from the second proximal opening 12b of the blood B flowing from the second distal opening 12a.

As shown in FIG. 3, the second lumen 12 is formed in the first region A1 and the second region A2 along the longitudinal direction of the tubular member 10. The second lumen 12 is formed over the first region A1 and the second region A2, and the second lumen 12 is longer than the first lumen 11. Here, the second region A2 is a region located on the proximal side of the first region A1 in the longitudinal direction of the tubular member 10. That is, the second region A2 is a region located on the proximal side relative to the first proximal opening 11b in the longitudinal direction of the tubular member 10. Therefore, the second lumen 12 extends from a predetermined position in the first region A1 to a position on the proximal side relative to the first proximal opening 11b in the longitudinal direction of the tubular member 10. For example, as shown in FIG. 3, the second lumen 12 extends from the second distal opening 12a located in the first region A1 to the proximal end of the tubular member 10.

The second distal opening 12a is located on the proximal side relative to the first distal opening 11a in the longitudinal direction of the tubular member 10. Similarly, to the first distal opening 11a, a center of the second distal opening 12a is formed at a position (eccentric position) deviated from the axial center of the tubular member 10.

As shown in FIG. 3, the second distal opening 12a preferably forms the inclined portion 12c inclined toward the distal side (first distal opening 11a) of the first lumen 11. In the adhesive material injection device 100, when the second distal opening 12a forms the inclined portion 12c, the tubular member 10 has a shape in which the outer diameter of the tubular member 10 decreases from the proximal end to a distal end of the inclined portion 12c and in which there is no corner portion protruding in an outer circumferential direction. Therefore, when the adhesive material injection device 100 is removed from the living body, a sliding resistance caused by catching on the subcutaneous tissue S or the like can be reduced while helping prevent damage to a living tissue around the second distal opening 12a.

Figures 5A, 5B:
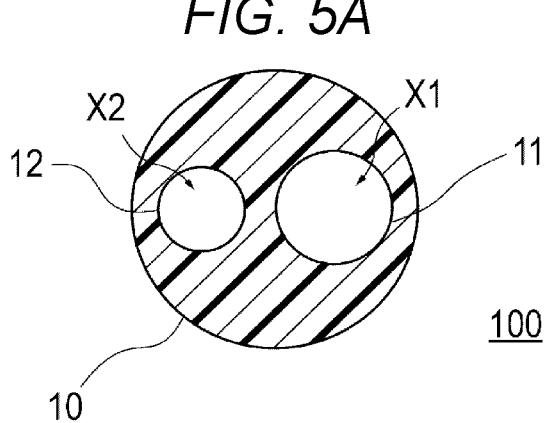
FIG. 5A is a cross-sectional view taken along an arrow II-II shown in FIG. 3.
FIG. 5B is a cross-sectional view taken along an arrow III-III shown in FIG. 3.

The tubular member 10 includes the first lumen 11 and the second lumen 12 in the first region A1. As shown in FIG. 5A, in the first region A1, a surface area of the second lumen 12 is smaller than a surface area of the first lumen 11 in the cross-section perpendicular to the longitudinal direction of the tubular member 10. That is, a ratio of the second lumen 12 to the cross-section perpendicular to the longitudinal direction of the tubular member 10 is smaller than a ratio of the first lumen 11 to the cross-section perpendicular to the longitudinal direction of the tubular member 10. Therefore, when the tubular member 10 is deformed, the second lumen 12 is less likely to be affected by the deformation of the tubular member 10 than the first lumen 11. Therefore, when the tubular member 10 is deformed, the second lumen 12 is less likely to be crushed than the first lumen 11. Accordingly, even when the tubular member 10 is deformed when the surgeon inserts the adhesive material injection device 100 into the blood vessel Bv, the adhesive material injection device 100 can help prevent the second lumen 12 from being crushed in the first region A1. Therefore, the surgeon can reliably check the leakage of the blood B by the second lumen 12 of the tubular member 10.

As shown in FIG. 5A, a cross-sectional area X2 of the second lumen 12 is preferably smaller than a cross-sectional area X1 of the first lumen 11 in the first region A1. Alternatively, the cross-sectional area X2 of the second lumen 12 may be larger than the cross-sectional area X1 of the first lumen 11 in the first region A1.

The tubular member 10 includes the second lumen 12 in the second region A2. As shown in FIG. 5B, a surface area of the second lumen 12 in the second region A2 is the same as the surface area of the second lumen 12 in the first region A1 in the cross-section perpendicular to the longitudinal direction of the tubular member 10. As described above, from a viewpoint of ease of manufacture of the tubular member 10, the second lumen 12 preferably has the same cross-sectional area in the first region A1 and the second region A2. Note that a cross-sectional area of the second lumen 12 in the second region A2 may be different from the cross-sectional area of the second lumen 12 in the first region A1.

Figure 6A:
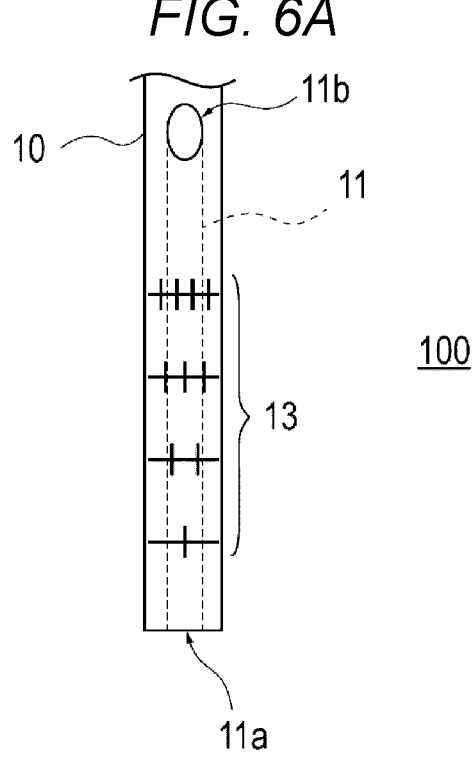
FIG. 6A is a view showing a form example of a first marker portion provided in the adhesive material injection device according to the present embodiment.

As shown in FIG. 6A, the tubular member 10 includes the first marker portion 13 indicating a distance from the first distal opening 11a to a predetermined position of the first lumen 11. The first marker portion 13 is provided on an outer surface of the tubular member 10 such that the surgeon can visually recognize the first marker portion 13. For example, the first marker portion 13 is provided on an outer peripheral surface in the vicinity of the distal end of the tubular member 10, and can be implemented, for example, by a colored portion, a figure, a symbol, a picture, an uneven shape, or the like. A specific configuration of the first marker portion 13 is not limited as long as the surgeon can grasp, by a visual sense or a tactile sense, a distance from the first distal opening 11a, orientation of the first proximal opening 11b in an outer circumferential direction of the adhesive material injection device 100, and the like. The surgeon can check the distance to the distal end (first distal opening 11a) of the tubular member 10 by checking a position of the first marker portion 13 of the tubular member 10 exposed to the outside of the living body. Therefore, when the surgeon retracts the adhesive material injection device 100 and searches for the discharge position of the adhesive material 200, the surgeon can rather easily grasp the accurate discharge position of the adhesive material 200 while checking the first marker portion 13. In addition, when the surgeon retracts the adhesive material injection device 100 from the blood vessel Bv to the proximal side, the surgeon can grasp how long the tubular member 10 is inserted into the living body by checking the first marker portion 13 exposed to the outside of the living body.

Hub Portion

The hub portion 20 includes a base portion 21 attached to an outer periphery of the tubular member 10, and a first engaging portion 22 connectable to a second engaging portion 421 of a sheath hub portion 420 on an outer peripheral surface of the base portion 21. The hub portion 20 is located in the second region A2 of the tubular member 10 and is provided between the first proximal opening 11b and the second proximal opening 12b. In the present embodiment, the first engaging portion 22 is implemented by a claw member including a hook-shaped portion at a distal end of the first engaging portion 22 and is fitted to the second engaging portion 421 of the sheath hub portion 420. Note that a form of the first engaging portion 22 is not limited to the claw member and may be any form having a complementary correlation with the second engaging portion 421.

The hub portion 20 can be connected to the sheath hub portion 420 of the introducer sheath 400 by the first engaging portion 22. Therefore, the adhesive material injection device 100 can be connected to the introducer sheath 400 via the hub portion 20 in a state where the tubular member 10 is inserted into a sheath lumen 411 of the introducer sheath 400. Accordingly, when adjusting a position of the first distal opening 11*a* of the adhesive material injection device 100, the surgeon can simultaneously move the adhesive material injection device 100 and the introducer sheath 400 by connecting the hub portion 20 and the sheath hub portion 420. For example, when the adhesive material injection device 100 is removed, a pulling operation can be rather easily performed simultaneously with the introducer sheath 400, and thus the procedure can be simplified. Note that in the adhesive material injection device 100, it is preferable that the pushing member 300 can be inserted into the first proximal opening 11*b* in a state where the hub portion 20 and the sheath hub portion 420 are connected to each other. Therefore, the first proximal opening 11*b* of the adhesive material injection device 100 is located on the distal side relative to a distal end of the introducer sheath 400 in the state where the hub portion 20 is connected to the sheath hub portion 420.

Stopcock

The stopcock 30 can include an operation lever 31, a first port 32, and a second port 33. The stopcock 30 is connected to the proximal end of the tubular member 10. A lumen of the stopcock 30 communicates with the second lumen 12 of the tubular member 10 via the second proximal opening 12*b*. The stopcock 30 can control, by a rotation operation of the operation lever 31, communication and non-communication between the first port 32 and the second lumen 12 and communication and non-communication between the second port 33 and the second lumen 12.

Therefore, the stopcock 30 can control a flow of the blood B passing through the second lumen 12 of the tubular member 10 and can control a flow of the blood B to an outside of the adhesive material injection device 100 via the second proximal opening 12*b*. The stopcock 30 may be provided, for example, with a multi-way stopcock having four or more ports instead of a three-way stopcock as shown in FIG. 1.

Inside the stopcock 30, a valve portion is provided for switching between the communication and non-communication between the first port 32 or the second port 33 and the second lumen 12 in conjunction with the rotation operation of the operation lever 31 in a predetermined direction. In the stopcock 30, the valve portion is moved by rotating the operation lever 31 in the predetermined direction, and the first port 32 and the second lumen 12 are in a state of communication (ON state). At this time, the second port 33 does not communicate with the second lumen 12. Further, in the stopcock 30, the valve portion is moved by rotating the operation lever 31 in the predetermined direction, and the second port 33 and the second lumen 12 are in a state of communication (ON state). At this time, the first port 32 does not communicate with the second lumen 12. When the first port 32 and the second lumen 12 are in the state of communication, the blood B flows in from the second distal opening 12*a*, passes through the second lumen 12, and leaks out of the living body from the first port 32.

A priming syringe or the like for priming the second lumen 12 can be connected to the second port 33 of the stopcock 30. Accordingly, the surgeon can prime the second lumen 12 with a saline solution (saline) or the like before inserting the adhesive material injection device 100 into the introducer sheath 400.

Note that the stopcock 30 may be implemented as a two-way stopcock that covers functions of the first port 32 and the second port 33 by a single port and can switch between the communication and non-communication between the port and the second lumen 12 by operating an operating lever.

Adhesive Material

The adhesive material 200 is a material capable of adhering to the puncture foramen P1 of the blood vessel Bv and is disposed in the first lumen 11 of the tubular member 10. For example, as shown in FIG. 3, the adhesive material 200 is held in the first lumen 11 in advance. Accordingly, the surgeon can save time and effort in loading the adhesive material 200 during the procedure, which can simplify the procedure.

Note that the adhesive material 200 is preferably disposed in the vicinity of the first distal opening 11*a*. Accordingly, since a distance by which the surgeon presses the adhesive material 200 with the pushing member 300 is reduced, the surgeon can discharge the adhesive material 200 to an indwelling position by the pushing member 300 with a relatively small force. Therefore, when the surgeon indwells the adhesive material 200 at a target position, the surgeon can rather easily discharge the adhesive material 200 to the target position because a positional deviation of the adhesive material injection device 100 caused by applying an excessive force to the pushing member 300 can be reduced.

The adhesive material 200 is pushed out from the first distal opening 11*a* by the pushing member 300 inserted from the first proximal opening 11*b*. Specifically, the surgeon can bring a distal end of the pushing member 300 into contact with the adhesive material 200 and move the adhesive material injection device 100 to the proximal side in a state of fixing a position of the pushing member 300, thereby helping prevent movement of the adhesive material 200 by the distal end of the pushing member 300 to discharge the adhesive material 200 from the first distal opening 11*a*. Therefore, when the adhesive material 200 is discharged from the first distal opening 11*a*, the surgeon moves the adhesive material injection device 100 to the proximal side in a state of fixing the position of the pushing member 300, and thus there is no need to push the adhesive material 200 toward the distal side of the tubular member 10 by the distal end of the pushing member 300. Therefore, the surgeon can accurately dispose the adhesive material 200 in the puncture foramen P1 formed in the blood vessel Bv while preventing the adhesive material 200 from being discharged into the blood vessel Bv.

Examples of a constituent material of the adhesive material 200 include a material that can be indwelled outside the blood vessel wall Bw to perform hemostasis on the puncture foramen P1. The adhesive material 200 can be formed of, for example, an adhesive material composition (liquid agent) such as cyanoacrylate and is not particularly limited as long as the adhesive material 200 is made of the material that can be indwelled outside the blood vessel wall Bw to perform hemostasis on the puncture foramen P1. The adhesive material 200 is held without leaking from the first lumen 11 until the surgeon performs a discharge operation. For example, in the adhesive material injection device 100, a sealed space can be formed in the first lumen 11 by two film-shaped sealing members, and the adhesive material 200 which is liquid can be held in the sealed space. In addition, in the adhesive material injection device 100, the adhesive material 200 accommodated in a bioabsorbable or biodegradable capsule can be loaded into the first lumen 11.

Pushing Member

The pushing member 300 can be implemented by a rod-shaped member and has an outer diameter such that the pushing member 300 can be inserted into the first lumen 11. The pushing member 300 is inserted into the first lumen 11 and pushes out the adhesive material 200 held in the first lumen 11. For example, as shown in FIG. 7G, the surgeon can use the pushing member 300 and indwell the adhesive material 200 outside the blood vessel wall Bw of the blood vessel Bv.

Figure 6B:
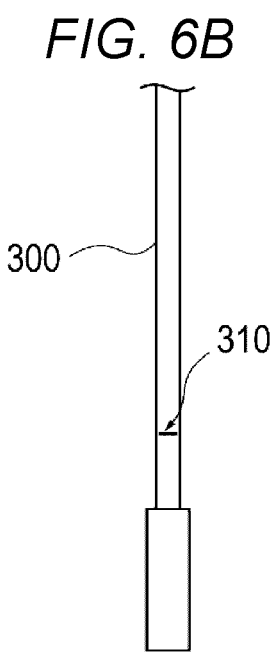
FIG. 6B is a view showing a form example of a second marker portion provided in a pushing member according to the present embodiment.

As shown in FIG. 6B, the pushing member 300 includes a second marker portion 310 for grasping an insertion amount when the pushing member 300 is inserted from the first proximal opening 11b. The second marker portion 310 is provided on an outer surface of the pushing member 300 such that the surgeon can visually recognize the second marker portion 310. For example, the second marker portion 310 can be provided on an outer peripheral surface of the pushing member 300 and can be, for example, implemented by a colored portion, a figure, a symbol, a picture, an uneven shape, or the like. A specific configuration of the second marker portion 310 is not limited as long as the surgeon can grasp, by the visual sense or the tactile sense, the insertion amount of the pushing member 300 into the first lumen 11. By providing the second marker portion 310 on the pushing member 300, the surgeon can grasp the insertion amount of the pushing member 300 into the first lumen 11, and therefore the surgeon can appropriately insert the pushing member 300.

Introducer Sheath

The introducer sheath 400 can be a hollow tubular member to be indwelled in the puncture site formed in the blood vessel Bv of the limb such as an arm of the patient for a purpose of inserting a guide wire, a catheter, or the like for treatment, examination, or the like into the blood vessel Bv. As shown in FIG. 7B, the adhesive material injection device 100 is introduced into the blood vessel Bv through the introducer sheath (introduction sheath) 400.

The introducer sheath 400 includes the sheath main body 410 having a lumen extending in the axial direction, and the sheath hub portion 420 connected to a proximal side of the sheath main body 410. The sheath main body 410 is a portion that is percutaneously introduced into the blood vessel Bv when the introducer sheath 400 is indwelled in the puncture site. Further, the sheath main body 410 can be implemented by a tubular member having a substantially cylindrical shape, and the sheath lumen 411 is formed in a lumen of the sheath main body 410. The sheath lumen 411 is a lumen extending from the distal end to a proximal end of the sheath main body 410. The sheath hub portion 420 is connectable to the hub portion 20 of the adhesive material injection device 100. The sheath hub portion 420 communicates with the sheath lumen 411 in the sheath hub portion 420.

The second engaging portion 421 connectable to the first engaging portion 22 of the hub portion 20 is provided in an outer peripheral surface of the sheath hub portion 420. In the present embodiment, the second engaging portion 421 can be implemented by a recessed groove formed along the outer peripheral surface of the sheath hub portion 420, and a distal end (hook-shaped portion) of the first engaging portion 22 of the hub portion 20 is fitted in the second engaging portion 421. Note that a form of the second engaging portion 421 is not limited to the recessed groove and may be any form having a complementary correlation with the first engaging portion 22.

As shown in FIG. 3, a hemostasis valve 422 is attached inside the sheath hub portion 420. As the hemostasis valve 422, a substantially elliptical film-shaped (disk-shaped) valve body formed of a silicone rubber, a latex rubber, a butyl rubber, or an isoprene rubber which is an elastic member can be used, and a form and a material of the valve are not particularly limited.

Treatment Method

Next, a treatment method using the adhesive material injection device 100 according to the present embodiment will be described with reference to FIGS. 7A to 7H. Note that in the following description, a series of flows of the treatment method will be described as an example, and the treatment method is not limited to a presented specific order.

Figure 7A:
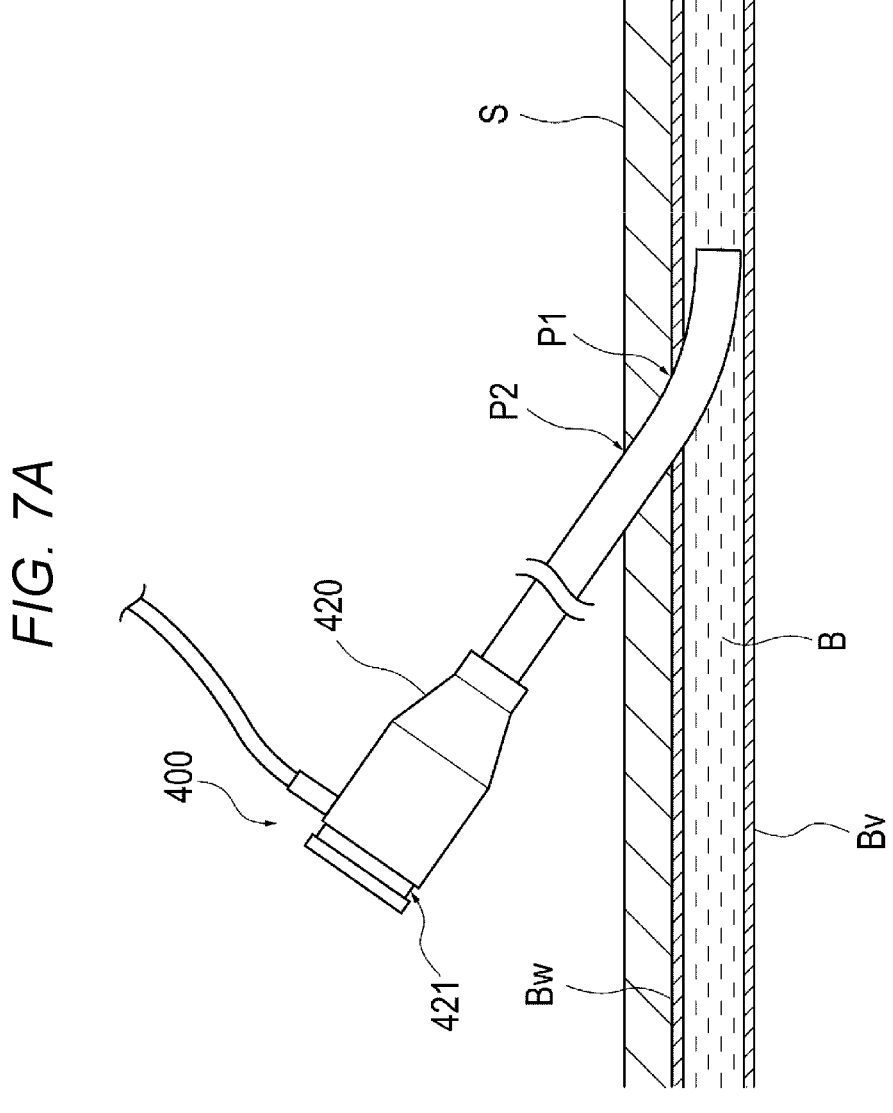
FIG. 7A is a schematic cross-sectional view illustrating a usage example of the adhesive material injection device according to the present embodiment.
Figure 7B:
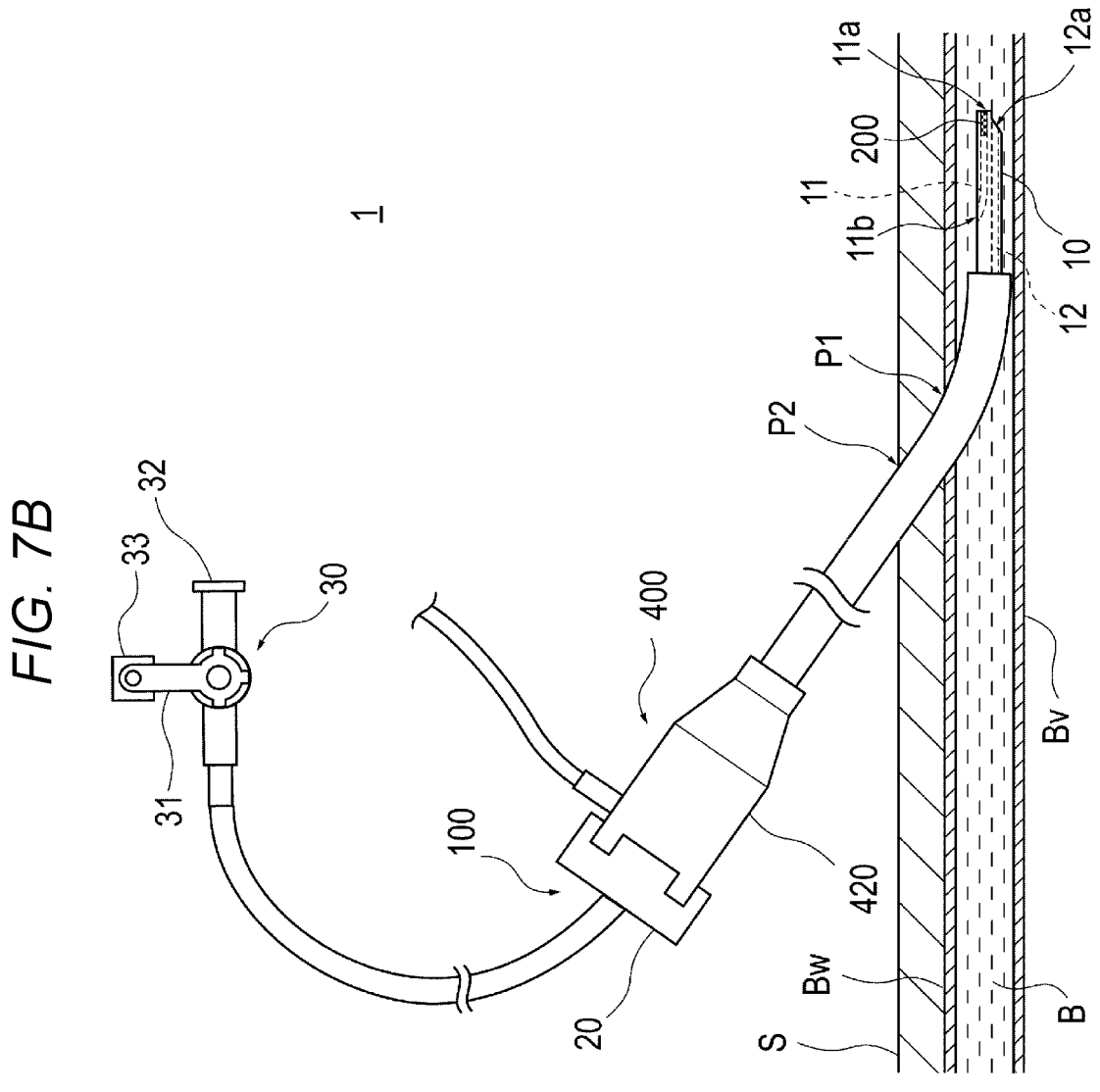
FIG. 7B is a schematic cross-sectional view illustrating a usage example of the adhesive material injection device according to the present embodiment.

FIG. 7A shows a state where the introducer sheath 400 is introduced into the blood vessel Bv from a skin of a patient. In the procedure described in the present embodiment, the introducer sheath 400 is inserted in a direction opposite to a direction in which blood flows in the blood vessel Bv. The surgeon can deliver various medical devices to a treatment target site of the patient via the introducer sheath 400 and perform treatment and diagnosis. Before the procedure use the introducer sheath 400, in order to introduce the sheath main body 410 of the introducer sheath 400 into the blood vessel Bv, the surgeon forms, in the subcutaneous tissue S, a puncture foramen P2 reaching the blood vessel wall Bw as the puncture site. Further, the surgeon forms the puncture foramen P1 as the puncture site in the blood vessel Bv located in the subcutaneous tissue S. The puncture foramens P1 and P2 formed in the puncture site of the patient are formed at an acute angle with respect to the blood vessel Bv from the skin tissue. Note that the blood vessel Bv can be, for example, a radial artery running in a wrist of the patient. However, the blood vessel Bv can be freely selected according to a content of the procedure and the like and is not particularly limited.

The surgeon prepares the adhesive material injection device 100 in advance in which the adhesive material 200 as shown in FIG. 1 is held in the first lumen 11. Accordingly, the time and effort in loading the adhesive material 200 during the procedure can be saved, which can simplify the procedure. When the adhesive material injection device 100 is prepared, in a case where the adhesive material 200 is not held in the first lumen 11 of the adhesive material injection device 100, the surgeon can dispose the adhesive material 200 in the first lumen 11.

As shown in FIG. 7B, after finishing a procedure using various medical devices, the surgeon inserts the adhesive material injection device 100 into the living body through the sheath main body 410 of the introducer sheath 400, and positions the first distal opening 11a, the first proximal opening 11b, and the second distal opening 12a in the blood vessel Bv. Before inserting the adhesive material injection device 100 into the introducer sheath 400, the surgeon primes the second lumen 12 with the saline solution or the like such that air does not enter the blood vessel Bv. The surgeon engages the first engaging portion 22 of the hub portion 20 with the second engaging portion 421 of the sheath hub portion 420 in a state where the adhesive material injection device 100 is inserted into the introducer sheath 400. Accordingly, the adhesive material injection device 100 is mounted on the introducer sheath 400. In the state where the adhesive material injection device 100 is mounted on the introducer sheath 400, the first region A1 of the tubular member 10 is located on the distal side relative to the introducer sheath 400. Therefore, the first distal opening 11a, the first proximal opening 11b, and the second distal opening 12a are located in the blood vessel Bv.

Figure 7C:
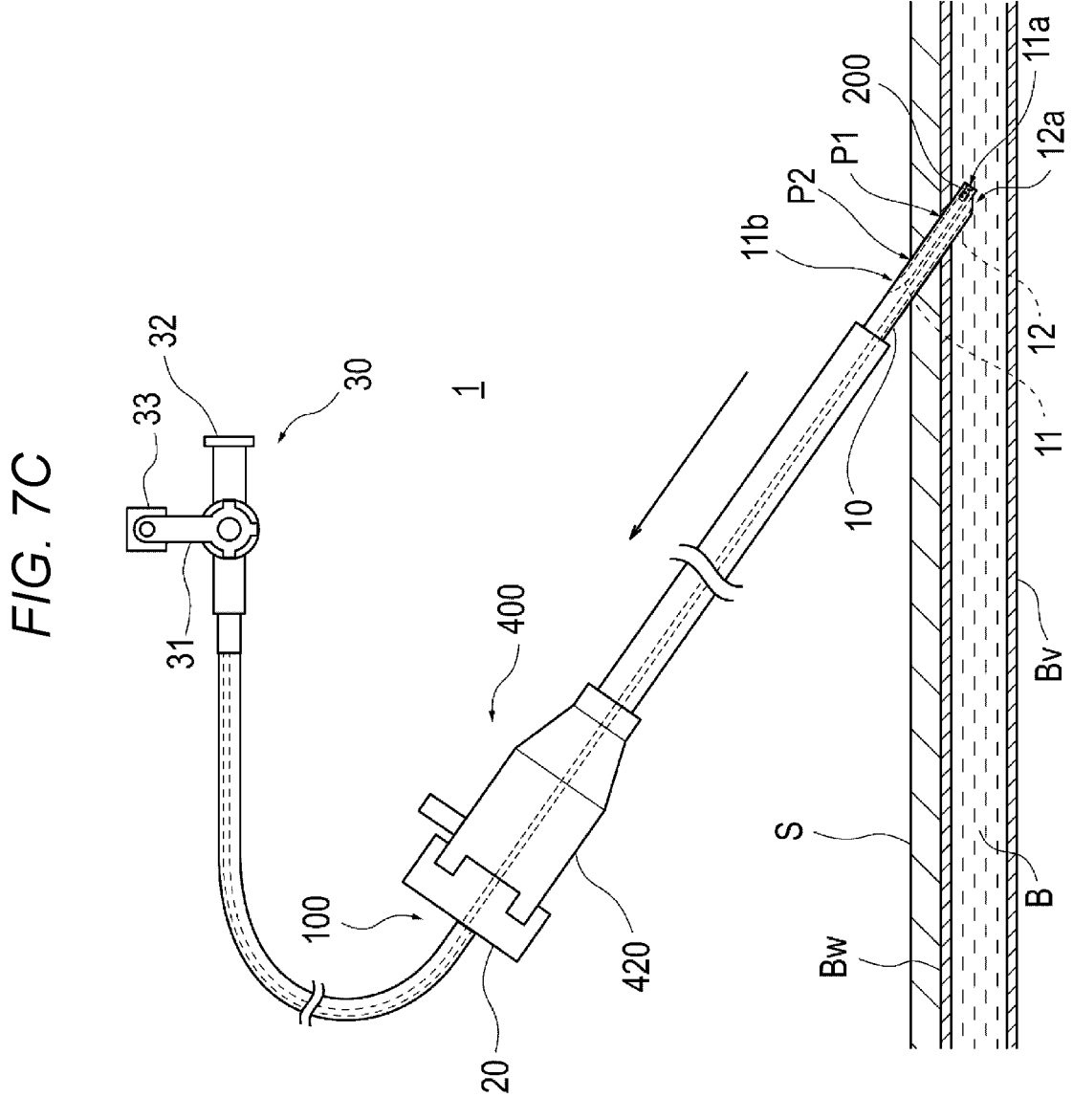
FIG. 7C is a schematic cross-sectional view illustrating a usage example of the adhesive material injection device according to the present embodiment.
Figure 7D:
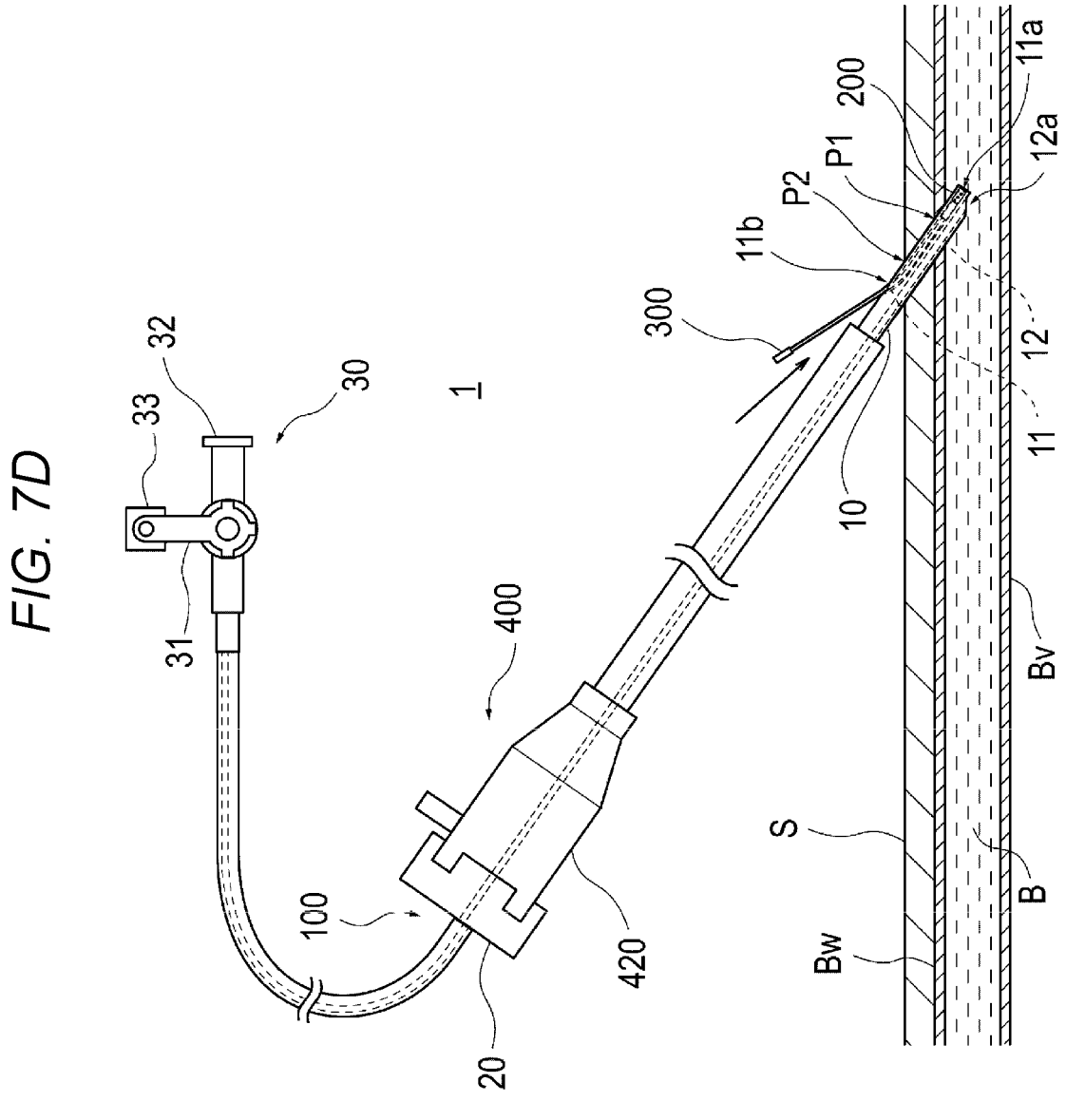
FIG. 7D is a schematic cross-sectional view illustrating a usage example of the adhesive material injection device according to the present embodiment.

Next, as shown in FIG. 7C, the surgeon moves the adhesive material injection device 100 to the proximal side such that the first proximal opening 11b is exposed to the outside of the living body. At this time, the adhesive material injection device 100 is connected to the introducer sheath 400 via the hub portion 20. Therefore, as shown in FIG. 7C, the surgeon can simultaneously move (retract) the adhesive material injection device 100 and the introducer sheath 400 toward the proximal side to expose the first proximal opening 11b to the outside of the living body. Accordingly, the surgeon can insert the pushing member 300 into the first proximal opening 11b exposed to the outside of the living body. Further, as shown in FIG. 7C, the first proximal opening 11b is moved to the outside of the living body, and the first distal opening 11a and the second distal opening 12a of the tubular member 10 are located in the blood vessel Bv.

Subsequently, as shown in FIG. 7D, the surgeon inserts the pushing member 300 into the first proximal opening 11b exposed to the outside of the living body. After inserting the pushing member 300 into the first lumen 11, the surgeon moves the pushing member 300 such that the distal end of the pushing member 300 is located near a proximal end of the adhesive material 200. At this time, the surgeon advances the pushing member 300 in a direction of the first distal opening 11a until the distal end of the pushing member 300 comes into contact with the proximal end of the adhesive material 200.

Figure 7E:
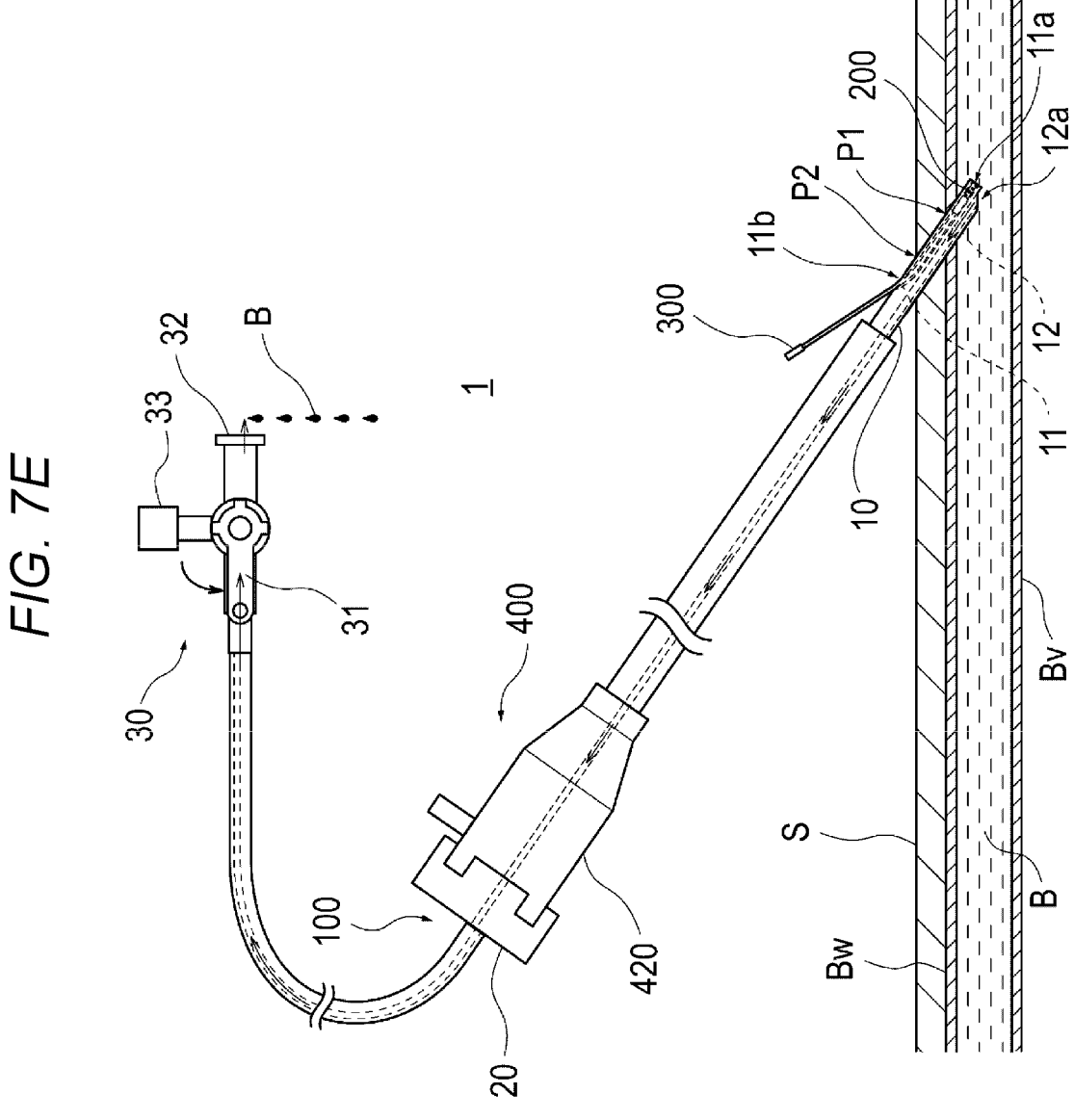
FIG. 7E is a schematic cross-sectional view illustrating a usage example of the adhesive material injection device according to the present embodiment.

Subsequently, as shown in FIG. 7E, the surgeon can check the blood B leaking from the second proximal opening 12b through the second lumen 12. At this time, the surgeon rotates the operation lever 31 of the stopcock 30 to bring the second lumen 12 and the first port 32 into communication with each other. Accordingly, when the second distal opening 12a is located in the blood vessel Bv, the blood B flowing into the second distal opening 12a from the blood vessel Bv leaks out of the living body through the first port 32 of the stopcock 30. Therefore, the surgeon can check the position of the second distal opening 12a by confirming that the blood B leaks from the first port 32 of the stopcock 30.

When the blood B does not leak out from the first port 32 in a state where the second lumen 12 and the first port 32 communicate with each other, the surgeon may advance the adhesive material injection device 100 toward the blood vessel Bv such that the second distal opening 12a is located in the blood vessel Bv. The surgeon can cause the blood B to flow into the second lumen 12 by advancing the adhesive material injection device 100 and moving the second distal opening 12a into the blood vessel Bv.

Figure 7F:
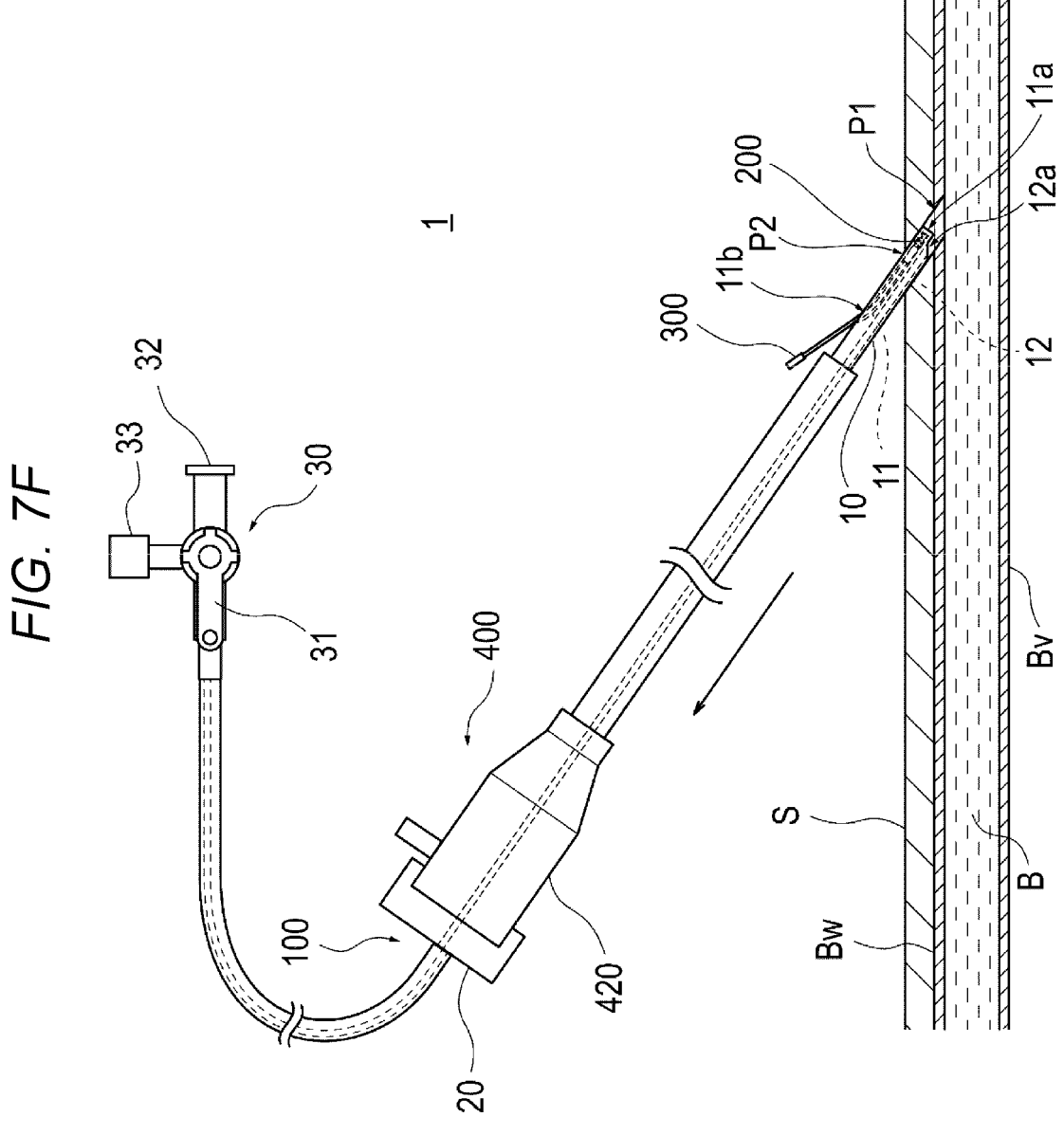
FIG. 7F is a schematic cross-sectional view illustrating a usage example of the adhesive material injection device according to the present embodiment.
Figure 7G:
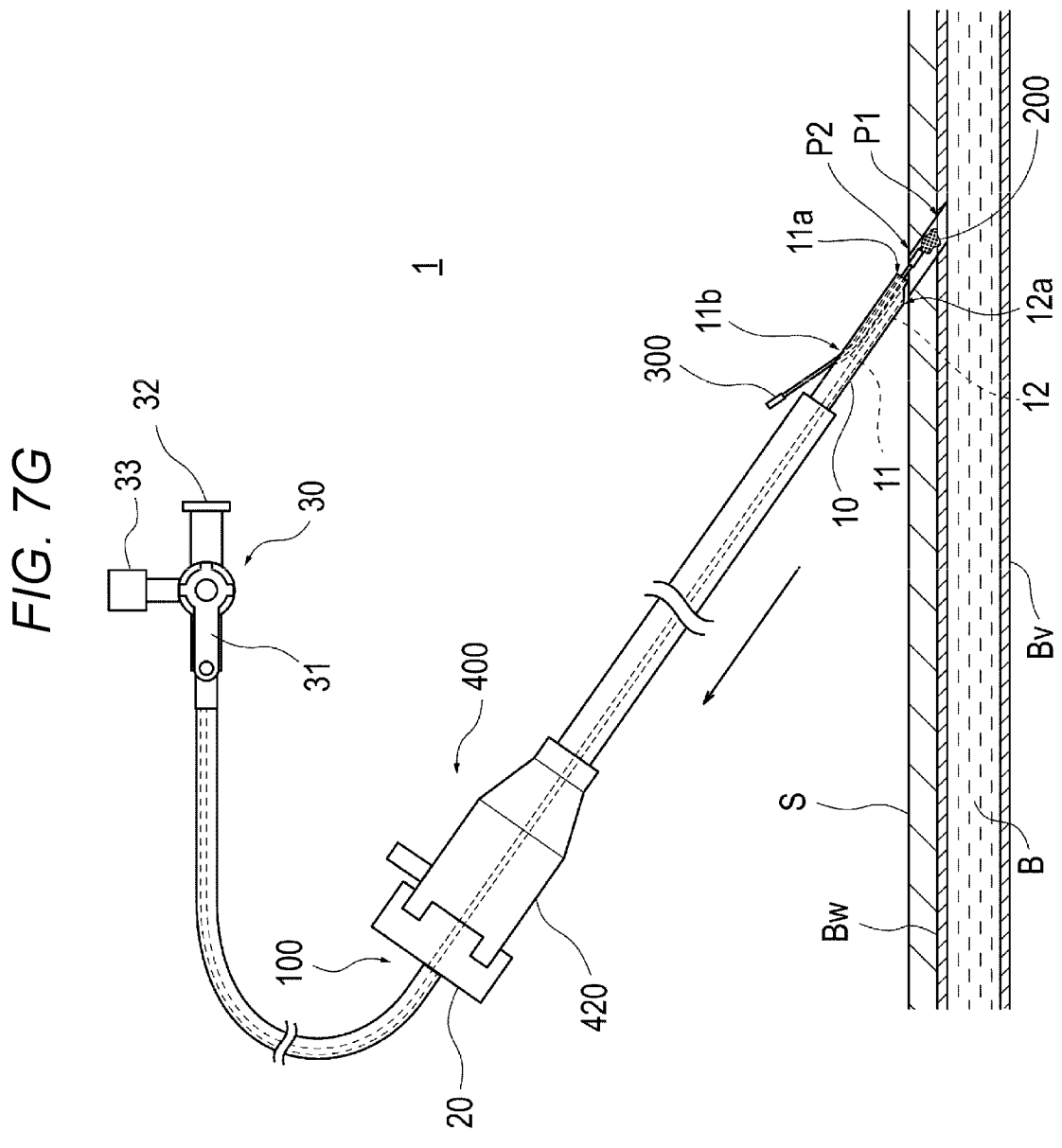
FIG. 7G is a schematic cross-sectional view illustrating a usage example of the adhesive material injection device according to the present embodiment.

Subsequently, as shown in FIG. 7F, the surgeon moves (retreats) the adhesive material injection device 100 to the proximal side to a position where the leakage of the blood B from the second proximal opening 12b stops while checking the blood B leaking from the second proximal opening 12b through the first port 32. At this time, since the introducer sheath 400 is connected to the adhesive material injection device 100 via the hub portion 20, the introducer sheath 400 moves to the proximal side simultaneously with the adhesive material injection device 100. When the adhesive material injection device 100 is disposed at the position where the leakage of the blood B from the second proximal opening 12b stops, the second distal opening 12a is located outside the blood vessel wall Bw. In the adhesive material injection device 100, when the second distal opening 12a is located outside the blood vessel wall Bw, the blood B stops leaking from the second proximal opening 12b through the first port 32 or a leakage amount of the blood B can be significantly reduced. Accordingly, the surgeon can grasp that the second distal opening 12a is disposed outside the blood vessel wall Bw by checking the blood B leaking from the second proximal opening 12b through the first port 32. Further, in the adhesive material injection device 100, when the second distal opening 12a is located outside the blood vessel wall Bw, the first distal opening 11a is located outside the blood vessel wall Bw. Therefore, the surgeon can dispose the first distal opening 11a outside the blood vessel wall Bw by retracting the adhesive material injection device 100 to the proximal side to the position where the leakage of the blood B from the second proximal opening 12b stops while checking the blood B leaking from the second proximal opening 12b through the first port 32.

The surgeon may advance and retract the adhesive material injection device 100 while checking the blood B leaking from the second proximal opening 12b through the first port 32. The surgeon can reliably grasp whether the second distal opening 12a is moved to the outside of the blood vessel wall Bw by moving the second distal opening 12a between an inside and the outside of the blood vessel Bv.

Subsequently, as shown in FIG. 7G, the surgeon moves (retreats) the adhesive material injection device 100 to the proximal side in a state where the position of the pushing member 300 is fixed such that the pushing member 300 does not move together with the adhesive material injection device 100. For example, the surgeon moves the adhesive material injection device 100 to the proximal side with a left hand while fixing the position of the pushing member 300 with a right hand. Accordingly, the adhesive material 200 is pressed by the distal end of the pushing member 300 and pushed out from the first distal opening 11a. Therefore, when the surgeon retreats the adhesive material injection device 100 to the proximal side, the adhesive material 200 is indwelled in the puncture foramen P1 serving as the puncture site formed in the blood vessel Bv. Since the introducer sheath 400 is connected to the adhesive material injection device 100 via the hub portion 20, the introducer sheath 400 can move to the proximal side simultaneously with the adhesive material injection device 100. When the adhesive material 200 is pushed out from the first distal opening 11a of the first lumen 11, the adhesive material 200 is indwelled (filled) in a predetermined range in a depth direction of the puncture foramen P2 of the subcutaneous tissue S from the outside of the blood vessel wall Bw. Accordingly, the surgeon can rather easily control a start position at which the adhesive material 200 is pushed out from the first distal opening 11a to the puncture foramen P1 and can reliably indwell the adhesive material 200 outside the blood vessel wall Bw. Therefore, the puncture foramen P1 of the blood vessel Bv can be safely blocked by the adhesive material 200.

As shown in FIGS. 7A to 7G, the adhesive material injection device 100 can be introduced into the blood vessel Bv through the introducer sheath 400, and hemostasis of the puncture site can be performed by a relatively simple operation. Therefore, the adhesive material injection device 100 can be used for puncture sites of various limbs using the introducer sheath 400. Therefore, the surgeon does not need to learn hemostasis methods corresponding to the puncture sites of various limbs and a method for using a device and can perform the hemostasis on the puncture site. Furthermore, in the adhesive material injection device 100, even when the indwelling position of the adhesive material 200 deviates from an appropriate position, the adhesive material 200 can be reindwelled by reloading the adhesive material 200 into the first lumen 11.

Figure 7H:
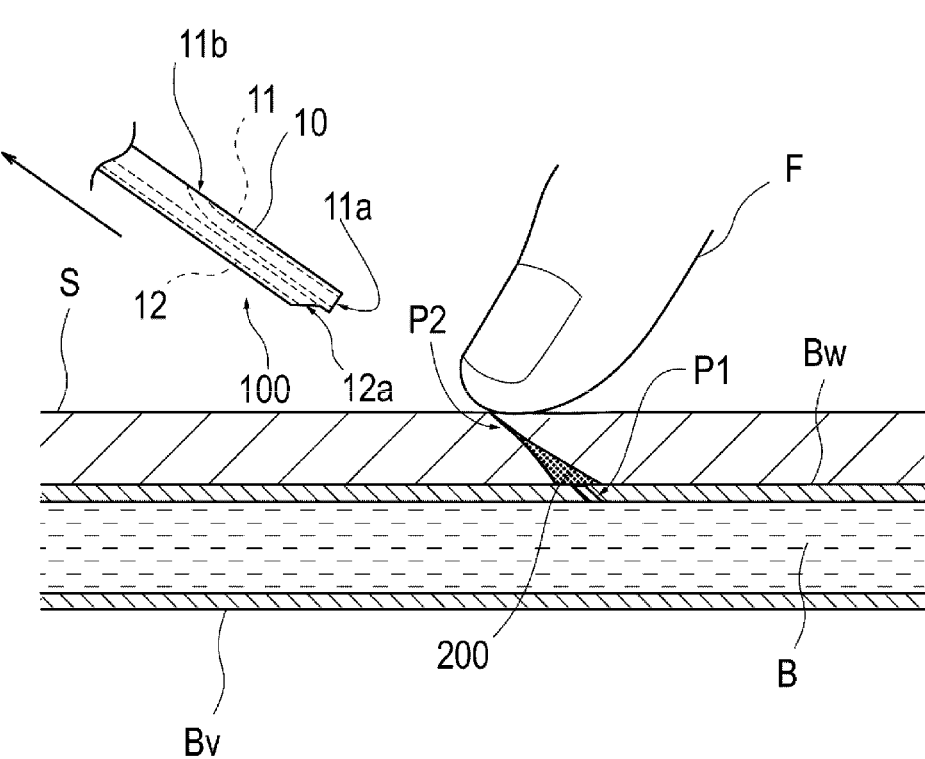
FIG. 7H is a schematic cross-sectional view illustrating a usage example of the adhesive material injection device according to the present embodiment and is an enlarged view of a puncture site of a blood vessel.

As shown in FIG. 7H, the surgeon removes the adhesive material injection device 100 from the living body and presses the vicinity of the puncture site from the living body surface layer side. For example, the surgeon removes the adhesive material injection device 100 connected to the introducer sheath 400 from the living body and presses the vicinity of the puncture foramen P2 with a finger F from the living body surface layer side. The surgeon can promote adhesion of the puncture foramen P2 formed in the subcutaneous tissue S by pressing the vicinity of the puncture foramen P2 with the finger F from the living body surface layer side. Accordingly, the surgeon can perform the hemostasis on the puncture foramens P1 and P2 serving as the puncture sites.

Functions and Effects

As described above, the adhesive material injection device 100 according to the present embodiment includes the tubular member 10 including a plurality of lumens, and the adhesive material 200 held in the lumen of the tubular member 10. The tubular member 10 includes the first lumen 11 extending between the first distal opening 11a and the first proximal opening 11b, and the second lumen 12 extending between the second distal opening 12a and the second proximal opening 12b at a position different from the first lumen 11. The first distal opening 11a is located on the distal side relative to the second distal opening 12a in the longitudinal direction of the tubular member 10. The adhesive material 200 is held in the first lumen 11 between the first distal opening 11a and the first proximal opening 11b.

According to the adhesive material injection device 100 implemented in this way, the tubular member 10 includes the first distal opening 11a and the second distal opening 12a located on the proximal side of the first distal opening 11a. The adhesive material 200 is held in the first lumen 11 extending between the first distal opening 11a and the first proximal opening 11b. Further, in the adhesive material injection device 100, the first distal opening 11a through which the adhesive material 200 can be discharged is located on the distal side relative to the second distal opening 12a through which the blood B can flow. The puncture foramens P1 and P2 formed in the puncture site of the patient to introduce the introducer sheath 400 are formed at the acute angle with respect to the blood vessel Bv from the skin tissue. Therefore, in the adhesive material injection device 100, in order to position the first distal opening 11a and the second distal opening 12a outside the puncture foramen P1 formed in the blood vessel Bv at the same timing in a state where the second distal opening 12a is located on the peripheral side of the blood vessel Bv relative to the first distal opening 11a, it can be necessary to position the first distal opening 11a on the distal side relative to the second distal opening 12a. According to the adhesive material injection device 100 having such a configuration, the surgeon can check the position of the second distal opening 12a while checking the leakage of the blood B from the second proximal opening 12b by introducing the adhesive material injection device 100 into the blood vessel Bv through the puncture site of the patient, disposing the first distal opening 11a and the second distal opening 12a of the tubular member 10 in the blood vessel Bv, and then retracting the adhesive material injection device 100 to the proximal side. Therefore, by confirming that the blood B leaks from the second proximal opening 12b of the tubular member 10, the surgeon can rather easily grasp whether the first distal opening 11a of the tubular member 10 is located inside the blood vessel wall Bw (in the blood vessel Bv) or outside the blood vessel wall Bw (in the subcutaneous tissue S). Therefore, since the surgeon can accurately grasp the discharge position of the adhesive material 200 with respect to the periphery of the puncture foramen P1 of the blood vessel Bv, the adhesive material 200 can be indwelled at an appropriate position with respect to the puncture foramen P1 formed in the blood vessel Bv.

In the adhesive material injection device 100, the tubular member 10 may have the first region A1 and the second region A2 located on the proximal side relative to the first region A1. The first lumen 11 may extend only in the first region A1, and the second lumen 12 may be longer than the first lumen 11 and extend over the first region A1 and the second region A2. The first proximal opening 11b may be located between the second distal opening 12a and the second proximal opening 12b.

According to the adhesive material injection device 100 implemented in this way, the first lumen 11 is shorter than the second lumen 12. The first proximal opening 11b is located between the first distal opening 11a and the second proximal opening 12b in the longitudinal direction of the tubular member 10. Therefore, the adhesive material injection device 100 can hold the adhesive material 200 in a region between the second distal opening 12a and the first proximal opening 11b of the tubular member 10 while reducing a length of the first lumen 11. In addition, in the adhesive material injection device 100, when the surgeon pushes out the adhesive material 200 through the first distal opening 11a, a distance by which the surgeon moves the adhesive material 200 in the first lumen 11 can be reduced. In the adhesive material injection device 100, since the length of the first lumen 11 is relatively small, the length of the pushing member 300 can also be relatively small. Therefore, the surgeon can efficiently transmit the pushing force to the adhesive material 200 using the pushing member 300 when pushing out the adhesive material 200 through the first distal opening 11a. Therefore, the operability of the surgeon can be improved.

In the adhesive material injection device 100, the cross-sectional area X2 of the second lumen 12 may be smaller than the cross-sectional area X1 of the first lumen 11 in the first region A1.

According to the adhesive material injection device 100 implemented in this way, the tubular member 10 includes the first lumen 11 and the second lumen 12 in the first region A1. In addition, the cross-sectional area X2 of the second lumen 12 is smaller than the cross-sectional area X1 of the first lumen 11 in the first region A1. That is, in the first region A1, the surface area of the second lumen 12 is smaller than the surface area of the first lumen 11 in the cross-section perpendicular to the longitudinal direction of the tubular member 10. Therefore, when the tubular member 10 is deformed, the second lumen 12 is less likely to be affected by the deformation of the tubular member 10 than the first lumen 11. Therefore, even in a state where the tubular member 10 is deformed, the surgeon can push out the adhesive material 200 through the first lumen 11 while reliably checking the leakage of the blood B through the second lumen 12 of the tubular member 10.

In the adhesive material injection device 100, the first proximal opening 11b may be provided in the side wall of the tubular member 10, and the tubular member 10 may have the curved region 11c that forms a part of the first lumen 11.

According to the adhesive material injection device 100 implemented in this way, the tubular member 10 has the curved region 11c that forms a part of the first lumen 11. Therefore, when the surgeon inserts the pushing member 300 from the first proximal opening 11b toward the first distal opening 11a and pushes out the adhesive material 200 by the pushing member 300, the curved region 11c supports a part of the pushing member 300 while changing orientation of the distal end of the pushing member 300. Therefore, the surgeon can rather easily transmit the pressing force when the adhesive material 200 is pushed out by the pushing member 300 to the pushing member 300, and the adhesive material 200 can be reliably discharged.

In the adhesive material injection device 100, the second distal opening 12a may form the inclined portion 12c inclined toward the first lumen 11.

According to the adhesive material injection device 100 implemented in this way, the second distal opening 12a forms the inclined portion 12c inclined toward the first lumen 11. Therefore, the outer diameter of the tubular member 10 decreases from the proximal end to the distal end of the inclined portion 12c. Therefore, when the adhesive material injection device 100 is removed from the living body, the sliding resistance caused by catching on the subcutaneous tissue S or the like can be reduced while helping prevent damage to the living tissue around the second distal opening 12a.

In the adhesive material injection device 100, the tubular member 10 may include the first marker portion 13 indicating a distance to the first distal opening 11a between the first distal opening 11a and the first proximal opening 11b.

According to the adhesive material injection device 100 implemented in this way, the tubular member 10 includes the first marker portion 13 indicating a position to the first distal opening 11a. Therefore, the surgeon can check the distance to the distal end (first distal opening 11a) of the tubular member 10 by checking the position of the first marker portion 13 of the tubular member 10 exposed to the outside of the living body. Therefore, the surgeon can relatively easily grasp the position of the first distal opening 11a and dispose the adhesive material 200 at an appropriate position.

In the adhesive material injection device 100, the tubular member 10 may include the hub portion 20 between the first proximal opening 11b and the second proximal opening 12b.

According to the adhesive material injection device 100 implemented in this way, the hub portion 20 is located between the first proximal opening 11b and the second proximal opening 12b. Therefore, the adhesive material injection device 100 can be operated integrally with the introducer sheath 400 by being connected to the introducer sheath 400 via the hub portion 20. Therefore, the surgeon can simultaneously move the adhesive material injection device 100 and the introducer sheath 400, and the procedure can be simplified. The hub portion 20 is located between the first proximal opening 11b and the second proximal opening 12b in the longitudinal direction of the tubular member 10. Therefore, the first proximal opening 11b can be exposed from the distal end of the sheath main body 410 when the adhesive material injection device 100 is connected to the introducer sheath 400 via the hub portion 20.

The adhesive material injection device 100 may include the pushing member 300 inserted from the first proximal opening 11b of the first lumen 11 to discharge the adhesive material 200 from the first distal opening 11a.

The adhesive material injection device 100 implemented in this way includes the dedicated pushing member 300 that can be inserted into the first proximal opening 11b and that can push out the adhesive material 200 from the first lumen 11. Therefore, when the surgeon uses the adhesive material injection device 100, the time and effort in pushing out the adhesive material 200 can be reduced.

In the adhesive material injection device 100, the pushing member 300 may include the second marker portion 310 indicating the insertion amount of the pushing member 300 into the first lumen 11.

According to the adhesive material injection device 100 implemented in this way, since the pushing member 300 includes the second marker portion 310 indicating the insertion amount of the pushing member 300 into the first proximal opening 11b, the surgeon can rather easily grasp the insertion amount of the pushing member 300 into the first lumen 11 via the second marker portion 310.

The medical instrument 1 according to the present embodiment includes the above-described adhesive material injection device 100 and the introduction sheath (introducer sheath 400) including the lumen (sheath lumen 411) into which the adhesive material injection device 100 can be inserted. The introducer sheath 400 includes the sheath hub portion 420 connectable to the hub portion 20. The adhesive material injection device 100 is implemented such that the first proximal opening 11b of the adhesive material injection device 100 is located on the distal side relative to the introducer sheath 400 in the state where the hub portion 20 is connected to the sheath hub portion 420.

According to the medical instrument 1 implemented in this way, the hub portion 20 of the adhesive material injection device 100 is connectable to the sheath hub portion 420 of the introducer sheath 400. Therefore, the surgeon can connect the hub portion 20 and the sheath hub portion 420 in the state where the adhesive material injection device 100 is inserted into the introducer sheath 400 indwelled in the blood vessel Bv. Therefore, since the surgeon can perform the pulling operation on the adhesive material injection device 100 simultaneously with the introducer sheath 400, the procedure can be simplified. The first proximal opening 11b is located on the distal side relative to the introducer sheath 400 in the state where the adhesive material injection device 100 is mounted on the introducer sheath 400. Therefore, the adhesive material injection device 100 is implemented such that, when the surgeon simultaneously retracts the adhesive material injection device 100 and the introducer sheath 400 to the proximal side, the introducer sheath 400 can be removed to the outside of the living body before the first proximal opening 11b of the tubular member 10 is exposed to the outside of the living body. Therefore, the surgeon can insert the pushing member 300 through the first proximal opening 11b exposed to the outside of the living body without worrying about a position of the introducer sheath 400. Accordingly, the surgeon can discharge the adhesive material 200 to the outside of the blood vessel wall Bw through the first distal opening 11a.

In the medical instrument 1, the adhesive material injection device 100 may include the pushing member 300 inserted from the first proximal opening 11b of the first lumen 11 to discharge the adhesive material 200 from the first distal opening 11a.

The medical instrument 1 implemented in this way includes the dedicated pushing member 300 that can be inserted into the first proximal opening 11b of the adhesive material injection device 100 and that can push out the adhesive material 200 from the first lumen 11. Therefore, in a case where the surgeon uses the medical instrument 1, when the pushing member 300 is inserted through the first proximal opening 11b of the tubular member 10 of the adhesive material injection device 100 exposed to the outside of the living body, the time and effort in pushing out the adhesive material 200 can be reduced.

In the medical instrument 1, the pushing member 300 may include the second marker portion 310 indicating the insertion amount of the pushing member 300 into the first lumen 11.

According to the medical instrument 1 implemented in this way, since the pushing member 300 includes the second marker portion 310 indicating the insertion amount of the pushing member 300 into the first proximal opening 11b, the surgeon can rather easily grasp the insertion amount of the pushing member 300 into the first lumen 11 via the second marker portion 310.

OTHER EMBODIMENTS

Figure 8:
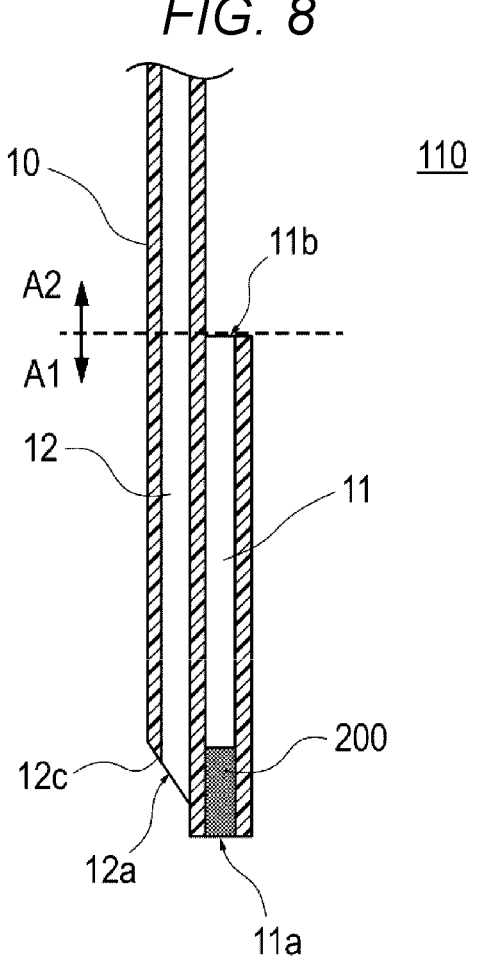
FIG. 8 is a schematic configuration diagram showing an adhesive material injection device according to a first modification.

Next, an adhesive material injection device 110 according to a modification will be described. In the modification, the redundant description of the contents already described will be omitted. In addition, in the modification, contents that are not particularly described have the same functions and the same effects as those of the above-described embodiment. First Modification FIG. 8 is a partial cross-sectional view of the adhesive material injection device 110 according to a first modification. The adhesive material injection device 110 according to the first modification is different from the adhesive material injection device 100 (see FIG. 3) according to the above-described embodiment in a formation position of the first proximal opening 11b with respect to the tubular member 10 and a structure of the first lumen 11.

The adhesive material injection device 110 is implemented such that the first lumen 11 extends substantially linearly along a longitudinal direction of the tubular member 10, and opening orientation of the first distal opening 11a and the first proximal opening 11b is oriented in the longitudinal direction. That is, the adhesive material injection device 110 does not have the curved region 11c forming a part of the first lumen 11 of the tubular member 10. In the adhesive material injection device 110, similarly to the above-described adhesive material injection device 100, the first lumen 11 extends only in the first region A1, and the second lumen 12 extends over the first region A1 and the second region A2.

In the adhesive material injection device 110 according to the first modification, since the first proximal opening 11b is opened along the longitudinal direction of the tubular member 10, the pushing member 300 can be rather easily inserted from the first proximal opening 11b. In addition, since the adhesive material injection device 110 can be pulled out along the pushing member 300 when being pulled out to a proximal side simultaneously with the introducer sheath 400, the pushing member 300 is not caught in the first lumen 11, and the adhesive material 200 can be relatively smoothly discharged.

The detailed description above describes embodiments of an adhesive material injection device. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. An adhesive material injection device comprising:
a tubular member including a first lumen extending between a first distal opening and a first proximal opening of the tubular member and a second lumen extending between a second distal opening and a second proximal opening of the tubular member at a position different from the first lumen, the tubular member includes a first region and a second region, the second region being located on a proximal side relative to the first region, the first lumen extends only in the first region, and the second lumen is longer than the first lumen and extends over the first region and the second region;
the first distal opening being located on a distal side relative to the second distal opening in a longitudinal direction of the tubular member, and wherein the first proximal opening is located between the second distal opening and the second proximal opening; and
an adhesive material configured to be held in the first lumen between the first distal opening and the first proximal opening.

2. The adhesive material injection device according to claim 1, wherein a cross-sectional area of the second lumen is smaller than a cross-sectional area of the first lumen in the first region.

3. The adhesive material injection device according to claim 1, wherein the first proximal opening is formed in a side wall of the tubular member, and the tubular member has a curved region forming a part of the first lumen.

4. The adhesive material injection device according to claim 1, wherein the second distal opening forms an inclined portion inclined toward the first lumen.

5. The adhesive material injection device according to claim 1, wherein the tubular member includes a first marker portion between the first distal opening and the first proximal opening, the first marker portion indicating a distance to the first distal opening.

6. The adhesive material injection device according to claim 1, further comprising:
a pushing member to be inserted from the first proximal opening of the first lumen to discharge the adhesive material from the first distal opening.

7. The adhesive material injection device according to claim 6, wherein the pushing member includes a second marker portion indicating an insertion amount of the pushing member into the first lumen.

8. The adhesive material injection device according to claim 1, wherein a distance from a position of an opening end of the second distal opening to a position of an opening end of the first distal opening is 2 mm to 5 mm.

9. The adhesive material injection device according to claim 1, wherein the tubular member includes a hub portion between the first proximal opening and the second proximal opening.

10. A medical instrument comprising:
the adhesive material injection device according to claim 9; and
an introduction sheath having a lumen into which the adhesive material injection device is configured to be inserted.

11. A medical instrument comprising:
an adhesive material injection device, the adhesive material injection device including a tubular member including a first lumen extending between a first distal opening and a first proximal opening of the tubular member and a second lumen extending between a second distal opening and a second proximal opening of the tubular member at a position different from the first lumen, the first distal opening being located on a distal side relative to the second distal opening in a longitudinal direction of the tubular member, and an adhesive material configured to be held in the first lumen between the first distal opening and the first proximal opening, and wherein the tubular member includes a hub portion between the first proximal opening and the second proximal opening;

an introduction sheath having a lumen into which the adhesive material injection device is configured to be inserted, the introduction sheath includes a sheath hub portion connectable to the hub portion; and the adhesive material injection device is implemented such that the first proximal opening of the adhesive material injection device is located on the distal side relative to the introduction sheath in a state where the hub portion is connected to the sheath hub portion.

12. The medical instrument according to claim 11, wherein the adhesive material injection device includes a pushing member to be inserted from the first proximal opening of the first lumen to discharge the adhesive material from the first distal opening.

13. The medical instrument according to claim 12, wherein the pushing member includes a second marker portion indicating an insertion amount of the pushing member into the first lumen.

14. The medical instrument according to claim 11, further comprising:

a pushing member to be inserted from the first proximal opening of the first lumen to discharge the adhesive material from the first distal opening, and wherein the pushing member includes a second marker portion indicating an insertion amount of the pushing member into the first lumen.

15. An adhesive material injection device comprising:

a tubular member including a first lumen extending between a first distal opening and a first proximal opening of the tubular member and a second lumen extending between a second distal opening and a second proximal opening of the tubular member at a position different from the first lumen, the tubular member includes a first region and a second region, the second region being located on a proximal side relative to the first region, and the second lumen is longer than the first lumen and extends over the first region and the second region;

the first distal opening is located on a distal side relative to the second distal opening in a longitudinal direction of the tubular member, the first proximal opening is located between the second distal opening and the second proximal opening, and a cross-sectional area of the second lumen is smaller than a cross-sectional area of the first lumen in the first region; and wherein the first lumen is configured to hold an adhesive material between the first distal opening and the first proximal opening.

16. The adhesive material injection device according to claim 15, wherein the first proximal opening is formed in a side wall of the tubular member, and the tubular member has a curved region forming a part of the first lumen.

17. The adhesive material injection device according to claim 15, wherein the second distal opening forms an inclined portion inclined toward the first lumen.

18. The adhesive material injection device according to claim 15 wherein the tubular member includes a first marker portion between the first distal opening and the first proximal opening, the first marker portion indicating a distance to the first distal opening.

19. The adhesive material injection device according to claim 15, wherein a distance from a position of an opening end of the second distal opening to a position of an opening end of the first distal opening is 2 mm to 5 mm.

* * * * *